US009750826B2

(12) United States Patent
Nam et al.

(10) Patent No.: US 9,750,826 B2
(45) Date of Patent: Sep. 5, 2017

(54) METHOD FOR PREPARING PATIENT-SPECIFIC GLIOBLASTOMA ANIMAL MODEL, AND USES THEREOF

(71) Applicant: SAMSUNG LIFE PUBLIC WELFARE FOUNDATION, Seoul (KR)

(72) Inventors: Do Hyun Nam, Seoul (KR); Ju Yuon Jin, Gyeonggi-do (KR); Kyeung Min Joo, Seoul (KR)

(73) Assignee: SAMSUNG LIFE PUBLIC WELFARE FOUNDATION, Seoul (KR)

( * ) Notice: Subject to any disclaimer, the term of this patent is extended or adjusted under 35 U.S.C. 154(b) by 3 days.

(21) Appl. No.: 14/409,668

(22) PCT Filed: Jun. 21, 2013

(86) PCT No.: PCT/KR2013/005513
§ 371 (c)(1),
(2) Date: Dec. 19, 2014

(87) PCT Pub. No.: WO2013/191512
PCT Pub. Date: Dec. 27, 2013

(65) Prior Publication Data
US 2015/0104391 A1 Apr. 16, 2015

(30) Foreign Application Priority Data

Jun. 21, 2012 (KR) ........................ 10-2012-0067017

(51) Int. Cl.
*A61K 49/00* (2006.01)
*A01K 67/027* (2006.01)
*A01K 67/00* (2006.01)

(52) U.S. Cl.
CPC ...... *A61K 49/0008* (2013.01); *A01K 67/0271* (2013.01); *A01K 2227/105* (2013.01); *A01K 2267/0331* (2013.01); *A01K 2267/0356* (2013.01)

(58) Field of Classification Search
None
See application file for complete search history.

(56) References Cited

U.S. PATENT DOCUMENTS

2010/0190252 A1* 7/2010 Mayer ................ C12N 5/0656
435/381

OTHER PUBLICATIONS

Broadley et al., Stem Cells; Mar. 2011, 29:452-461.*
Mamoru et al., Blood Nov. 2002, 100 (9) 3175-3182.*
The Japanese Office Action for corresponding Japanese Patent Application No. 2015-518340; mailed Mar. 29, 2016; 4 pages.
Fei et al., "Open Access Research Development of clinically relevant orthotopic xenograft mouse model of metastatic lung cancer and glioblastoma through surgical tumor tissues injection with trocar", Journal of Experimental & Clinical Cancer Research, Jun. 29, 2010 (Jun. 29, 2010), p. 84, XP055239438, Retrieved from the Internet: URL: http://www.ncbi.nlm.nih.gov/pmc/articles/PMC2907866/pdf/1756-9966-29-84.pdf [retrieved on Jan. 7, 2016].
Tentler et al., "Patient-derived tumour xenografts as models for oncology drug development", Nature Reviews Clinical Oncology vol. 9, No. 6, Apr. 17, 2012 (Apr. 17, 2012), p. 338-350, XP021067032, NY, US ISSN: 1759-4774, DOI: 10.1038/nrclinonc. 2012.61.
Jian et al., "A reproducible brain tumour model established from human glioblastoma biopsies", BMC Cancer, Biomed Central, London, GB, vol. 9, No. 1, Dec. 29, 2009 (Dec. 29, 2009), p. 465, XP021067032, ISSN 1471-2407, DOI:10.1186/1471-2407-9-465.
Sarkaria et al., "Use of an orthotopic xenograft model for assessing the effect of epidermal growth factor receptor amplification on glioblastoma radiation response", Clinical Cancer Research, The American Association for Cancer Research, US, vol. 12, No. 71, Apr. 1, 2006 (Apr. 1, 2006), pp. 2264-2271, XP008116821, ISSN 1078-0432, DOI: 10.1158/1078-0432.CCR-05-2510 [retrieved on Apr. 1, 2006].
Jacobs et al., "Current review of in vivo GBM rodent models: emphasis on the CNS-1 tumour model", ASN Neuro, vol. 3, No. 3, Aug. 3, 2011 (Aug. 3, 2011), pp. 171-181, XP055239439, DOI: 10.1042/AN20110014.
Joo et al., "Patient-Specific Orthotopic Glioblastoma Xenograft Models Recapitulate the Histopathology and Biology of Human Glioblastomas In Situ", Jan. 17, 2013 (Jan. 17, 2013), XP055239385, Retrieved from the Internet: URL:http://www.sciencedirect.com/science/article/pii/S2211124712004585 [retrieved on Jan. 7, 2016].
Joo et al., "Clinical and biological implications of CD133-positive and CD133-negative cells in glioblastomas", Laboratory Investigation, Aug. 2008, vol. 88, No. 8, Jun. 16, 2008 (Jun. 16, 2008), pp. 808-815, XP055032074, ISSN 0023-6837, DOI: 10.1038/labinvest. 2008.57.
Oh et al., "Translational Validation of Personalized Treatment Strategy Based on Genetic Characteristics of Glioblastoma", PLOS ONE, vol. 9, No. 8, Aug. 1, 2014 (Aug. 1, 2014), p. e103327, XP055239606, DOI: 10.1371/journal.pone.0103327.
Lee et al., "Facilitating tailored therapeutic strategies for glioblastoma through an orthotopic patient-derived xenograft platform", Nov. 18, 2015 (Nov. 18, 2015), XP055239209, Retrieved from the Internet: URL:http://www.hh.um.es/Reviews-proofs/11-695-manuscript.pdf [retrieved on Jan. 7, 2016].
The European Search Report for corresponding European Patent Application No. 13 807 259.0, mailed Feb. 1, 2016, 9 pages.

* cited by examiner

*Primary Examiner* — Doug Schultz
(74) *Attorney, Agent, or Firm* — Vorys, Sater, Seymour & Pease LLP; Mih Suhn Koh

(57) ABSTRACT

Provided is a method for producing a glioblastoma mouse model and the mouse model produced thereby, the method including the steps of: (a) dividing a glioblastoma tissue, isolated from a patient, into 4 or more sections, and collecting one or more pieces from each of the sections; (b) dissociating a mixture of the collected pieces into glioblastoma cells as single cells; and (c) orthotopically transplanting a graft sample containing the glioblastoma cells obtained in step (b), into the brain of an immunodeficient mouse. Further provided are a method of screening a glioblastoma therapeutic agent using the mouse model and a method of providing information for selection of a patient-specific glioblastoma therapy using the mouse model. The glioblastoma mouse model shows the same genetic, morphological and pathological characteristics as those of the parental tumor, and it allows screening patient-specific glioblastoma therapeutic agent or selecting safer and more effective patient-specific glioblastoma therapy.

5 Claims, 10 Drawing Sheets

SEQUENCE LISTING

<160> NUMBER OF SEQ ID NOS: 10

<210> SEQ ID NO 1
<211> LENGTH: 19
<212> TYPE: DNA
<213> ORGANISM: Artificial
<220> FEATURE:
<223> OTHER INFORMATION: primer

<400> SEQUENCE: 1
ttcacttgtg ccctgactt                                    19

<210> SEQ ID NO 2
<211> LENGTH: 19
<212> TYPE: DNA
<213> ORGANISM: Artificial
<220> FEATURE:
<223> OTHER INFORMATION: primer

<400> SEQUENCE: 2
ctgggcaacc agccctgtc                                    19

<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3
accatgagcg ctgctcagat                                   20

```
<210> SEQ ID NO 4
<211> LENGTH: 22
<212> TYPE: DNA
<213> ORGANISM: Artificial
<220> FEATURE:
<223> OTHER INFORMATION: primer

<400> SEQUENCE: 4
agttgcaaac cagacctcag gc                                              22

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
cttgccacag gtctccccaa                                                 20

<210> SEQ ID NO 6
<211> LENGTH: 25
<212> TYPE: DNA
<213> ORGANISM: Artificial
<220> FEATURE:
<223> OTHER INFORMATION: primer

<400> SEQUENCE: 6
gaggctgggg cacagcaggc cagtg                                           25

<210> SEQ ID NO 7
<211> LENGTH: 20
<212> TYPE: DNA
<213> ORGANISM: Artificial
<220> FEATURE:
<223> OTHER INFORMATION: primer

<400> SEQUENCE: 7
actgcctctt gcttctcttt                                                 20

<210> SEQ ID NO 8
<211> LENGTH: 20
<212> TYPE: DNA
<213> ORGANISM: Artificial
<220> FEATURE:
<223> OTHER INFORMATION: primer

<400> SEQUENCE: 8
aagtgaatct gaggcataac                                                 20

<210> SEQ ID NO 9
<211> LENGTH: 19
<212> TYPE: DNA
<213> ORGANISM: Artificial
<220> FEATURE:
<223> OTHER INFORMATION: primer

<400> SEQUENCE: 9
cggtcttcag agaagccat                                                  19

<210> SEQ ID NO 10
<211> LENGTH: 22
<212> TYPE: DNA
<213> ORGANISM: Artificial
<220> FEATURE:
<223> OTHER INFORMATION: primer
```

```
<400> SEQUENCE: 10
gcaaaatcac attattgcca ac                                                22
```

METHOD FOR PREPARING PATIENT-SPECIFIC GLIOBLASTOMA ANIMAL MODEL, AND USES THEREOF

The Sequence Listing submitted in text format (.txt) filed on Dec. 19, 2014, named "PF-B1430_ST25.txt", created on Dec. 16, 2014, 4.0 KB), is incorporated herein by reference.

TECHNICAL FIELD

The present invention relates to a method for producing a glioblastoma mouse model, comprising the steps of: (a) dividing a glioblastoma tissue, isolated from a patient, into or more sections, and collecting one or more pieces from each of the sections; (b) dissociating a mixture of the collected pieces into glioblastoma cells as single cells; and (c) orthotopically transplanting a graft sample, which contains the glioblastoma cells obtained in step (b), into the brain of an immunodeficient mouse; a glioblastoma mouse model produced by the method; a method for screening a glioblastoma therapeutic agent using the mouse model; and a method for providing information for selection of a patient-specific glioblastoma therapy using the mouse model.

BACKGROUND ART

Gliomas are malignant tumors accounting for about 60% of primary brain tumors, have high incidence and are difficult to treat. Thus, effective treatment methods other than radiotherapy for gliomas have not yet reported. Among gliomas, glioblastoma (GBM) classified as the most malignant form has a very high resistance to radiotherapy and chemotherapy compared to other cancers, and thus life expectancy after diagnosis of glioblastoma is only one year. However, in the case of such brain tumors, the delivery of therapeutic drugs is not easy due to the presence of blood-brain barriers. Particularly, because of the insufficient understanding of brain neurobiology, the development of therapeutic agents is slowly progressing. Further, glioblastoma represents an aggressive variant compared to other brain tumors, and thus can cause lethal results within several weeks, if it is not treated within a short time. Treatment of glioblastoma is performed by radiotherapy and chemotherapy in addition to surgical therapy. However, because chemotherapy has reached its limit due to the occurrence of resistant variants, recurrence caused by tumor stem cells, etc, there is a need to develop new therapy.

In recent years, with the rapid development of systems biology and bioinformatics tools, genetic defects and gene expression patterns, which are considered to be associated with the development and progression of glioblastoma, have been reported. However, the screening of molecular markers that can represent clinical results is still insufficient. Particularly, gene expression analysis is performed at the transcriptome level, and thus cannot indicate the expression level of protein in actual cancer tissue. As a solution to this problem, the use of an animal model that best mimics glioblastoma has been proposed. This animal model can be used to study the development and progress of glioblastoma. Moreover, it can be used for the investigation of a new therapeutic strategy for glioblastoma and studies on a suitable combination of existing therapeutic strategies. In addition, it is expected to be used to examine the effects of new antitumor substances showing therapeutic effects against glioblastoma.

Accordingly, immune-compromised model animals such as nude mice have been used, or studies have been actively conducted to develop a glioblastoma-induced animal model. For example, the production of an animal model by transplantation of human glioblastoma was reported (Diao Yi, et al., Cancer Investigation, 29:229-239, 2011, EGFR Gene Overexpression Retained in an Invasive Xenograft Model by Solid Orthotopic Transplantation of Human Glioblastoma Multiforme Into Nude Mice). In the above paper, a mouse model was produced using only a graft sample prepared from the piece of a specific portion (single portion) of patient-derived glioblastoma, and thus there was difficulty in producing a glioblastoma mouse model showing the same genetic, morphological and pathological characteristics as those of the parental tumor. In addition, in a process for preparing a sample for preparing a graft sample for transplantation into a mouse according to the prior art, protease was used for enzymatic degradation of a tissue collected from a patient, but in this case, there is difficulty in separating the tissue into single cells, due to the viscosity of the tissue. Moreover, the Ficoll gradient method was generally used to remove erythrocytes from a graft sample collected from a patient, but in this case, there was a problem in that the efficiency with which blood is removed is low.

In order to treat a glioblastoma patient, the genetic, physiological and environmental characteristics of the patient should be taken into consideration, and various therapies, including chemotherapy, radiotherapy and surgical therapy, should be applied depending on the degree of progression of glioblastoma. However, because the above-described animal model cannot reflect the individual characteristics of a glioblastoma patient, it is merely used for the development of therapeutic methods or agents, and the actual use thereof for patient-specific treatment was limited. It is expected that, if an animal model that can best mimic the genetic and physiological conditions of each patient, the success rate of treatment can be greatly increased by performing a treatment specific for each patient.

Under such circumstances, the present inventors have made extensive efforts to establish a glioblastoma mouse model showing the same genetic, morphological and pathological characteristics as those of a glioblastoma patient, and as a result, have found that, when a graft sample, prepared from a mixture of glioblastoma tissue pieces, collected from various portions of glioblastoma tissue isolated from a glioblastoma patient, is orthotopically transplanted into the brain of a mouse, a glioblastoma mouse model showing the same genetic, morphological and pathological characteristics as those of the parental tumor can be established. In addition, the present inventors have developed the optimum conditions for establishing this mouse model, thereby completing the present invention.

DISCLOSURE OF INVENTION

The present invention provides a method for producing a glioblastoma mouse model, comprising the steps of: (a) dividing a glioblastoma tissue, isolated from a patient, into or more sections, and collecting one or more pieces from each of the sections; (b) dissociating a mixture of the collected pieces into glioblastoma cells as single cells; and (c) orthotopically transplanting a graft sample, which contains the glioblastoma cells obtained in step (b), into the brain of an immunodeficient mouse. The present invention also provides a mouse model produced by the above method, a method of screening a glioblastoma therapeutic agent using the mouse model, and a method of providing information for selection of a patient-specific glioblastoma therapy using the mouse model. The patient-specific glioblastoma mouse model according to the present invention shows the same genetic, morphological and pathological characteristics as those of the parental tumor, and thus it makes possible to screen a patient-specific glioblastoma therapeutic agent or select a safe and effective patient-specific glioblastoma therapy.

BEST MODE FOR CARRYING OUT THE INVENTION

Figure 1:
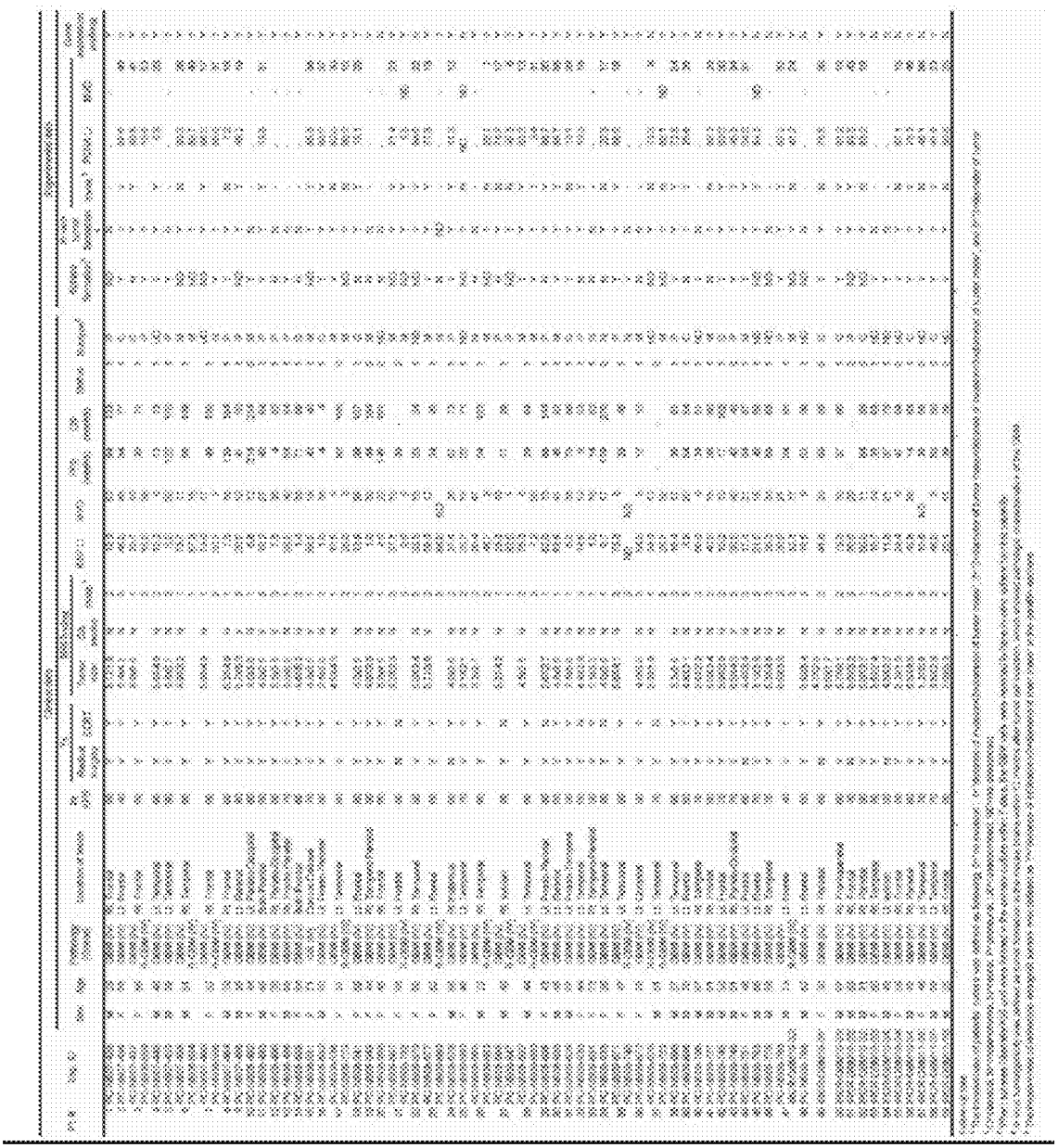
FIG. 1 shows the clinical data of glioblastoma patients, and experimental results for primarily cultured glioblastoma (GBM) cells derived from the patients.

It is an object of the present invention to provide a glioblastoma mouse model showing the same genetic, morphological and pathological characteristics as those of the parental tumor, and a method for producing the same.

Another object of the present invention is to screen a patient-specific glioblastoma therapeutic agent using the mouse model produced according to the present invention.

Still another object of the present invention is to provide a method of providing information for selection of a patient-specific glioblastoma therapy using the mouse model produced according to the present invention.

To achieve the above objects, the present invention provides a method for producing a glioblastoma mouse model, comprising the steps of: (a) dividing a glioblastoma tissue, isolated from a patient, into 4 or more sections, and collecting one or more pieces from each of the sections; (b) dissociating a mixture of the collected pieces into glioblastoma cells as single cells; and (c) orthotopically transplanting a graft sample, which contains the glioblastoma cells obtained in step (b), into the brain of an immunodeficient mouse.

The present invention also provides a method for screening a glioblastoma therapeutic agent, the method comprising a step of treating the above glioblastoma mouse model or glioblastoma cells derived therefrom with a candidate therapeutic agent.

The present invention also provides a method for providing information for selection of a patient-specific glioblastoma therapy, the method comprising the steps of: (a) subjecting the above glioblastoma mouse model to a candidate glioblastoma therapy; and (b) examining a therapeutic effect and prognosis while breeding the animal model subjected to the candidate therapy.

Unless defined otherwise, all technical and scientific terms used herein have the same meaning as commonly understood by one of ordinary skill in the art to which the invention pertains. Generally, the nomenclature used herein and the experiment methods are those well known and commonly employed in the art.

As used herein, the term "glioblastoma (GBM)" refers to a tumor derived from glial cells that are abundantly present in normal brain tissue. Specifically, glioblastoma is the most common single tumor of the brain, which makes up 12-15% of brain tumors and 50-60% of gliomas. In addition, it shows various symptoms, including headache (severe in the morning) caused by a rapid increase in brain pressure, nausea, vomiting, convulsions, a decrease in neural function caused by cerebral edema, a decrease in limb movement or sensibility, facial palsy, language disorder, cognitive impairment, and right-left discrimination disorder. To treat glioblastoma, TMZ (temozolomide)-based therapy and the like have been used. However, even when the same therapy is applied to glioblastoma patients, the therapeutic effect thereof can differ between the patients, because the patients have different genetic and pathologic conditions. For this reason, the development of a glioblastoma xenograft mouse model that reflects the genetic, physiological and pathological conditions of a patient has been required to screen glioblastoma therapeutic agents. Accordingly, the present inventors have developed a method of producing an orthotopic glioblastoma xenograft mouse model, which shows the same characteristics as those of the parental tumor, by orthotopically transplanting a graft sample, prepared from a glioblastoma tissue isolated from a patient, into the brain of a mouse. Particularly, when a mouse model is produced using only a portion of isolated cancer tissue based on the principle in which glioblastoma consists of genetically identical cancer cells, the mouse model will not show properly the characteristics of the parental tumor. To overcome this shortcoming, the present inventors have developed a method of producing a graft sample by dividing glioblastoma tissue into four or more sections, collecting pieces having a specific volume from the sections, and mixing the collected pieces with one another. Using this graft sample, a glioblastoma mouse model was produced. In other words, in the present invention, only a portion of a glioblastoma tissue was not transplanted into a mouse, but a sample prepared by mixing various portions of a glioblastoma tissue isolated from a patient was transplanted into a mouse, thereby producing a glioblastoma xenograft mouse that can completely reflect the characteristics of the patient. In the present invention, this orthotopic xenograft mouse that reflects the characteristics of the patient was named "avatar mouse".

In one aspect, the present invention is directed to a method for producing a glioblastoma mouse model, comprising the steps of: (a) dividing a glioblastoma tissue, isolated from a patient, into 4 or more sections, and collecting one or more pieces from each of the sections; (b)

dissociating a mixture of the collected pieces into glioblastoma cells as single cells; and (c) orthotopically transplanting a graft sample, which contains the glioblastoma cells obtained in step (b), into the brain of an immunodeficient mouse.

Steps (a) and (b) in the method for producing the orthotopic xenograft mouse for glioblastoma according to the present invention are steps of preparing a graft sample containing glioblastoma cells for producing a patient-specific glioblastoma mouse model.

As used herein, the term "graft sample containing glioblastoma cells" refers to a sample which is prepared from an isolated glioblastoma tissue of a glioblastoma patient in order to transplant it into the brain of a mouse, and which contains glioblastoma cells as single cells. The glioblastoma cells contained in the sample are preferably those derived from an isolated glioblastoma tissue of a glioblastoma patient within 3 hours after isolation of the glioblastoma tissue, but are not limited thereto. In addition, the sample is preferably prepared by dividing a glioblastoma tissue, isolated from a glioblastoma patient, into 4 or more sections, and collecting one or more pieces from each of the sections, so that it can properly reflect the characteristics of glioblastoma tumor of the patient. When a mouse model is produced using a graft sample prepared by dividing a glioblastoma tissue, isolated from a patient, into 4 or more sections, collecting one or more pieces from each of the sections, and mixing the collected pieces with one another to prepare a mixture containing glioblastoma cells, as described above, it can properly reflect the characteristics of glioblastoma tumor of the patient, unlike a mouse model prepared using a graft sample prepared from a tissue isolated from only a single specific portion. Thus, as disclosed in the present invention, a graft sample is preferably prepared by dividing a glioblastoma tissue into 4 or more sections, collecting one or more pieces from each of the sections, and mixing the collected pieces with one another. If pieces are collected from 4 or more sections, it is possible to produce a mouse model that shows the same genetic, morphological and pathological characteristics as those of the parental tumor. Thus, the upper limit of the number of the sections is not set, but pieces may be collected from 100 or less sections, because an increase in the number of sections leads to an increase in times and expenses.

Preferably, one or more pieces, each having a volume of 1-8 mm$^3$, may be collected from 4 or more sections. In addition, the volume of the mixture of the pieces collected in step (b) may preferably be 30-100% of the volume of the glioblastoma tissue isolated from the patient.

In addition, step (b) is a step of dissociating the mixture of the collected pieces into single cells. In this step, the mixture of the collected pieces can be dissociated into single cells by sequentially performing mechanical dissociation and enzymatic dissociation of the mixture.

The mechanical dissociation process can be performed using any conventional device known in the art. In an example of the present invention, a dissociator was used. The sample subjected to the mechanical dissociation process may be subjected to an enzymatic dissociation process. A reagent that is used in this enzymatic dissociation preferably includes both protease and DNase. Examples of the protease include, but are not limited to, cysteine protease such as papain, and examples of the DNase include, but are not limited to, DNase I. The present inventors have found that, when DNase is used in addition to protease when the enzymatic dissociation process is performed, it is effective in solving problems associated with the increase in viscosity caused by performing the homogenization process. Thus, the enzymatic dissociation process is preferably performed using a reagent including both protease and DNase. The sample subjected to the enzymatic dissociation process as described above may optionally be filtered, after examining whether the sample was dissociated into single cells.

The filtration process may be performed using any filter having a pore size suitable for separation of single cells. In an example of the present invention, a single cell population was obtained using a cell strainer.

After the filtration process as described above, the sample comprising the single cell-type glioblastoma cells may be subjected to a process of removing blood from the sample. This blood removal process may be performed using any conventional erythrocyte removal method known in the art, but is preferably performed by Percoll gradient centrifugation. In an example of the present invention, it was found that the efficiency with which blood was removed was higher when the Percoll gradient centrifugation method was used, compared to when the Ficoll gradient centrifugation method was used.

Step (b) of the method of the present invention is a step of orthotopically transplanting the sample, which contains glioblastoma cells obtained in step (b), into the brain of an immunodeficient mouse.

As used herein, the term "immunodeficient mouse" refers to a mouse obtained by artificially damaging part of the immune system at the gene level to make the immune system abnormal so as to develop glioblastoma. The immunodeficient mouse that is used in the present invention may be a mouse having a nervous system formed therein. Preferably, it may be a mouse engineered to be immunodeficient. In the prior art, nude mice were mainly used, but when NOG (NOD/SCID Il2rg$^{-/-}$) mice are used to produce the mouse model, there is an advantage in that the rate of production of the mouse model is further increased. Thus, most preferably, NOG (NOD/SCID Il2rg$^{-/-}$) mice may be used in the present invention.

The graft sample containing glioblastoma cells is characterized in that it is orthotopically transplanted into the brain of an immunodeficient mouse.

Transplantation of the graft sample into the mouse brain may be performed by injecting the sample into the mouse brain at the location of 1.5-2.5 mm left and 0.5-1.5 mm anterior to the bregma and 1.8-2.2 mm deep from the dura. The inventive method comprising orthotopically transplanting the sample into the mouse brain has an advantage in that it can easily maintain the characteristics of the parental tumor, compared to the case of transplanting glioblastoma into the mouse flank.

In addition, when the graft sample of step (a) is orthotopically transplanted into the mouse brain, the sample preferably contain $1 \times 10^5$-$5 \times 10^5$ glioblastoma cells and has a volume of 5-15 µl. If the cell number of the sample is about $10^4$ or less or about $10^6$ or more, the rate of production of the glioblastoma mouse disease model can be reduced.

When the transplanted cells grow and glioblastoma is formed within several weeks or several months after transplantation to establish a glioblastoma mouse disease model, a visible reduction in weight, tachypnea, palsy or other similar symptoms will appear. In an example of the present invention, among xenograft animal models, animals showing a decrease in weight of 20% or more were regarded as established disease models.

The inventive glioblastoma xenograft mouse model produced as described above has the genetic, morphological and molecular characteristics similar to those of the parental tumor that is a glioblastoma developed from the patient from the transplanted tissue was derived.

In another aspect, the present invention is directed to a glioblastoma mouse model produced by the glioblastoma mouse model producing method according to the present invention.

Even patients having the same glioblastoma have different characteristics, and thus therapeutic effects and prognosis can differ between the patients. Thus, when the same therapeutic method is applied to all patients having glioblastoma, the therapeutic effect thereof can differ between the patients. Thus, it is required to select a patient-specific and more effective therapeutic method from among various glioblastoma therapeutic methods or to screen a new therapeutic method. The patient-specific glioblastoma mouse model according to the present invention properly reflects the characteristics of the patient from which the glioblastoma cells were derived, and thus the use thereof makes it possible to select a therapeutic method suitable for the patient.

Specifically, the mouse model of the present invention is characterized in that the morphological characteristics such as invasiveness, proliferation index and microvessel density thereof are the same as or similar to those of the parental tumor. For example, the genetic environment such as either whether or not a gene encoding EGFR (Epidermal growth factor receptor), CDK2 (Cyclin-dependent kinase 2), PDGFRA (Alpha-type platelet-derived growth factor receptor), MDM2 (murine double minute), MDM4, MET (met proto-oncogene), CDK6 (Cyclin-dependent kinase 6), PIK3CA (phosphoinositide-3-kinase, catalytic, alpha polypeptide), and AKT3(RAC-gamma serine/threonine-protein kinase) is amplified, or whether or not a gene encoding CDKN2A/B (Cyclin-dependent kinase inhibitor 2A/B), PTEN (Phosphatase and tensin homology, CDKN2C (Cyclin-dependent kinase 4 inhibitor C), RB1 (retinoblastoma protein), PARK2 (parkinson protein 2), and NF1 (Neurofibromin 1) is deleted is the same as or similar to that of the parental tumor; and MBP (Myelin basic protein), PDGFA (Platelet-derived growth factor subunit A), EGFR, CHI3L1 (Chitinase-3-like protein 1), MAP2 (Microtubule-associated protein 2), TOP2A (DNA topoisomerase 2-alpha), DLL3 (Delta-like 3), SOX2 (SRY(sex determining region Y)-box 2), and Olig2 (Oligodendrocyte transcription factor 2), which are known as marker proteins of glioblastoma, can be expressed to at a level that is the same as or similar to that of the parental tumor, but is not particularly limited thereto.

Figure 5:
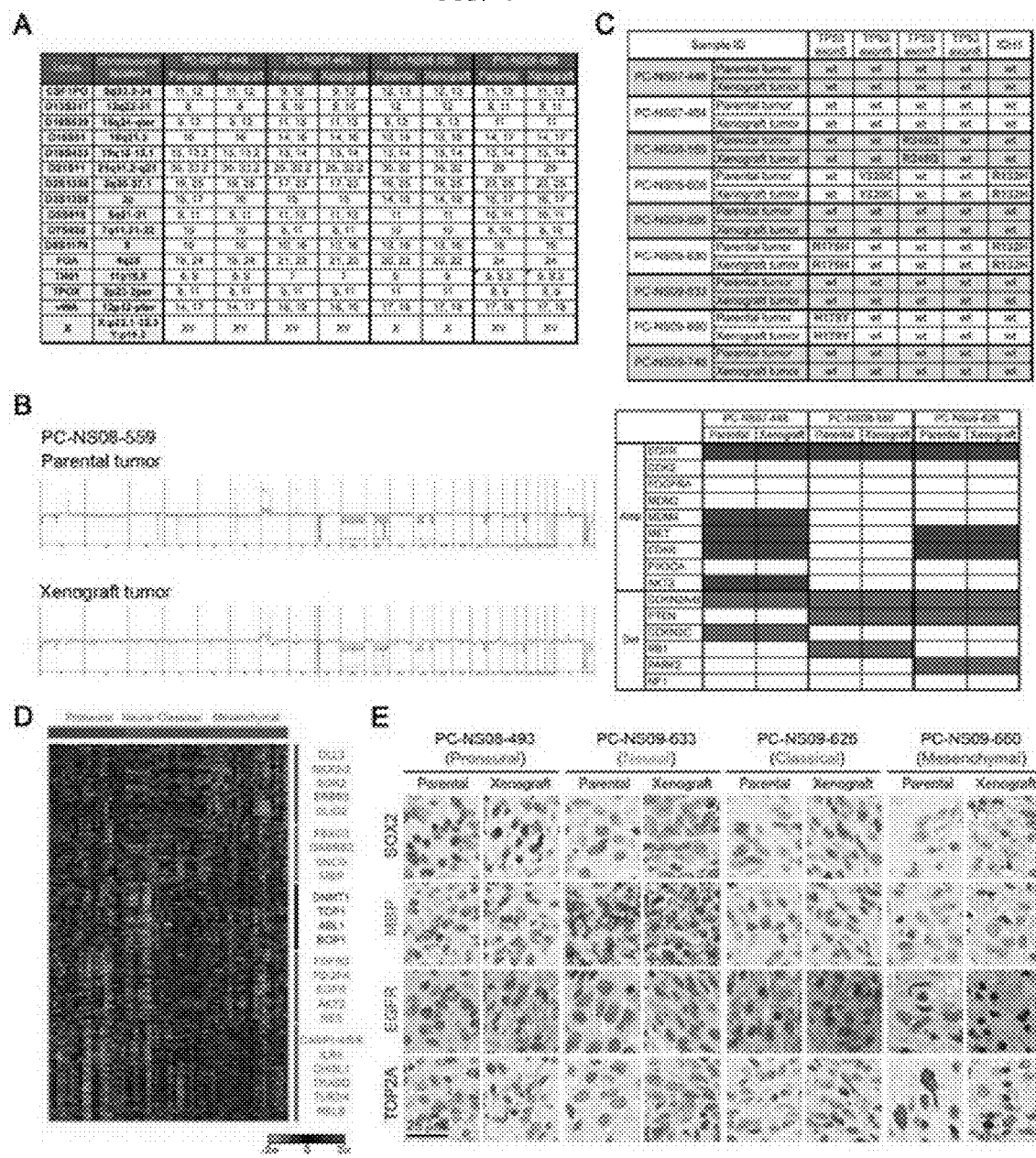
FIG. 5 shows the molecular characteristics of parental and orthotopic xenograft tumors. Short tandem repeat (A), genomic copy number variation (B), genetic mutation of TP53 and IDH1 (C), and gene expression pattern (D and E) of parental GBMs were compared with those of the corresponding orthotopic xenograft tumors. (B) Genomic copy number variation was analyzed by aCGH (left), and the genomic copy number variations of the genes that were reported to be altered frequently in GBMs were summarized (amplified: gray column; deleted: gray column). (C) Specific mutations were indicated by bold letters. wt: wild-type. (D) Subtypes of 58 GBM samples were determined by the Nearest Template Prediction method. (E) Expression of gene products was compared immunohistochemically between parental GBMs and corresponding orthotopic xenograft tumors.

In an example of the present invention, various portions of a glioblastoma tissue isolated from a glioblastoma patient were evenly cut within 3 hours after isolation so that the cells of the various portions of the whole tumor tissue could be evenly mixed. Then, the tissue was dissociated into single cells by mechanical dissociation and enzymatic dissociation, and 10 µl of HBSS solution containing $1.0 \times 10^5$ to $2.0 \times 10^5$ glioblastoma cells was transplanted into the mouse brain (2 mm left and 1 mm anterior to the bregma, and 2 mm from the dura). When a mouse showed a decrease in weight of 20% or more, it was regarded to have glioblastoma, and was sacrificed (Example 2). Then, the morphological and pathological similarities between the produced patient-specific glioblastoma mouse model and its parental tumor were examined. Specifically, the invasiveness, the proliferation index and the vessel intensity were examined, and as a result, it was shown that the invasiveness, the proliferation index and the microvessel density were all closely similar between the parental tumor and the mouse model transplanted with the glioblastoma derived therefrom (Experimental Example 2). In addition, genomic similarity was examined, and as a result, it was shown that the copy number and the genetic mutation were consistent between the mouse model and its parental tumor (FIGS. 5B and 5C). Further, the gene expression was examined by a microarray, and as a result, it was shown that the parental tumor and the corresponding xenograft tumor showed similar gene expression characteristics (FIG. 5E). Whether the mouse model of the present invention properly reflects the morphological, pathological and genetic characteristics of its parental tumor was examined, and then whether the response of the mouse model to glioblastoma therapies is similar to that of the parental tumor was examined. As a result, the mouse model and the parental tumor showed similar tendencies in both radiotherapy and TMZ-based chemotherapy (Experimental Example 4). The above results suggest that the glioblastoma mouse model produced by the method of the present invention sufficiently reflects the characteristics of the patient from which the transplanted glioblastoma was derived, and thus it is useful as a platform for selecting a patient-specific therapeutic agent and therapeutic method.

In another aspect, the present invention is directed to a method for screening a glioblastoma therapeutic agent, the method comprising a step of treating the above glioblastoma mouse model or glioblastoma cells derived therefrom with a candidate therapeutic agent.

The screening method may further comprise a step of examining the therapeutic effect of the candidate therapeutic agent against the mouse model or glioblastoma cells derived therefrom.

The therapeutic effect of the candidate therapeutic agent can be determined by administering the candidate therapeutic agent into the mouse by a suitable route such as an oral, intravenous or transdermal route, and then measuring the size of a tumor, the degree of metastasis and the dead cell/living cell ratio. Particularly, the inventive glioblastoma mouse model or glioblastoma cells derived therefrom reflect the characteristics of the patient from which the glioblastoma was derived, and thus can be effectively used for selection of a therapeutic agent suitable for the patient.

In addition, the screening method may further comprise a step of determining the prognosis of the mouse model treated with the candidate therapeutic agent. As used herein, the term "prognosis" means the prediction of progression of disease or recovery from disease. In the present invention, the prognosis refers to evaluating whether the candidate agent can treat glioblastoma developed in a patient, by examining the degree of progression of the glioblastoma after administering the candidate agent into a mouse.

As described above, the use of the glioblastoma mouse model produced according to the present invention makes it possible to predict the progression of glioblastoma or recovery from glioblastoma upon the application of a candidate agent or therapy to glioblastoma patients.

In still another aspect, the present invention is directed to a method for providing information for selection of a patient-specific glioblastoma therapy, the method comprising the steps of: (a) subjecting the above glioblastoma mouse model to a candidate glioblastoma therapy; and (b) examining a therapeutic effect and prognosis while breeding the animal model subjected to the candidate therapy.

Herein, the glioblastoma and the mouse model are as described above.

In the information providing method, step (a) is a step of performing a candidate glioblastoma therapy on the glioblastoma mouse model of the present invention.

As used herein, the term "candidate therapy" means various therapies from which a patient-specific therapy for treating a glioblastoma developed in the patient can be selected. The candidate therapy may be any possible method known to be used to treat glioblastoma, and examples thereof include chemotherapy, radiotherapy, surgical therapy, immune cell therapy, and combinations thereof.

As used herein, the term "chemotherapy" refers to a method of treating glioblastoma by administering a conventional candidate therapeutic agent having anticancer activity to the patient. As used herein, the term "radiotherapy" refers to a method of treating glioblastoma by treating the patient with radiation, and the term "surgical therapy" refers to a method of treating glioblastoma by surgically removing a portion having the glioblastoma.

The term "immune cell therapy" refers to a method of treating glioblastoma in a patient by separating immune cells, which attack glioblastoma, from monocytes extracted from the peripheral blood of the patient, fusing the selected cells with glioblastoma cells isolated from the patient, and administering the fused cells again into the patient in the form of anticancer vaccines. Herein, the immune cells that attack glioblastoma are preferably dendritic cells, but are not particularly limited thereto.

Although the following examples illustrate only the culture of neural stem cells of human origin in the medium of the present invention, it will be obvious to those skilled in the art that the culture of adult stem cells of other origins shows the same effect.

EXAMPLES

Hereinafter, the present invention will be described in further detail with reference to examples. It will be obvious to a person having ordinary skill in the art that these examples are illustrative purposes only and are not to be construed to limit or change the scope of the present invention. Also, those skilled in the art will appreciate that various modifications, additions and substitutions are possible based on this illustration, without departing from the scope and spirit of the invention.

Example 1

Glioblastoma (GBM) Patients and the Primary Culture of Cell Cultures Derived from the Patients Following informed consent, surgical samples and clinical records were obtained from 58 GBM patients who had brain tumor removal surgery at the Samsung Medical Center (Seoul, Korea), and data thereon are shown in FIG. 1. Specifically, FIG. 1 shows the clinical data of glioblastoma patients and experimental results for primarily cultured glioblastoma (GBM) cells derived from the patients.

The obtained surgical samples were classified as GBM based on WHO criteria by examination of pathologists. Parts of the surgical samples were enzymatically dissociated into single cells, and the dissociated GBM cells were cultured in the "NBE" condition. Specifically, the dissociated GBM cells were cultured in Neurobasal media with N2 and B27 supplements (0.53× each; Invitrogen) and bFGF and EGF (25 ng/ml each; R&D Systems). Alternatively, acutely dissociated GBM cells in the NBE condition were plated on the flasks, coated with Laminin (Sigma) overnight at 10 mg/ml prior to use, for the adherent culture.

Example 2

Construction of Orthotopic Xenograft Mouse Model

Animal experiments were approved by the Institutional Review Boards of the Samsung Medical Center and conducted in accordance with the "National Institutes of Health Guide for the Care and Use of Laboratory Animals" (NIH publication 80-23), and an orthotopic xenograft mouse model was produced in the following manner.

The production of the orthotopic xenograft mouse model was largely divided into the steps of: 1) preparing a sample (to be transplanted into a mouse) from a glioblastoma tissue isolated from a glioblastoma patient; and 2) transplanting the sample into a mouse. The procedure for the production of the orthotopic xenograft mouse model was as follows.

(1) Step of Preparing Homogenized Graft Sample from Tissue Isolated from Glioblastoma Patient A sample to be transplanted into a mouse was prepared using a fresh tissue within 2-3 hours after isolation from a glioblastoma patient, and the preparation was performed in the order shown in Table 1 below.

TABLE 1

| Order | Procedure |
|---|---|
| 1 | Tissue homogenization |
| 2 | Tumor tissue dissociation (mechanical dissociation and enzymatic dissociation) |
| 3 | Filtration of single cells |
| 4 | Removal of erythrocytes |
| 5 | Calculation of cell number and viability |

Specifically, the glioblastoma tissue isolated from the patient was divided into 4 or more sections, and at least one piece having a volume of 1-8 mm$^3$ was collected from each of the sections using scissors and forceps so that the collected pieces had a volume corresponding to 30-80% of the volume of the isolated glioblastoma tissue, and thus the cells of various portions of the whole tumor tissue could be evenly mixed.

During establishment of the mouse model production procedure, the present inventors found that, when various portions of the whole tumor tissue were cut evenly and used to prepare the graft sample, the rate of production of the mouse model increased, and the mouse model had the genetic, morphological and marker-expressing characteristics similar to those of the patient and could best mimic the genetic and physiological characteristics of the patient, compared to when the mouse model was produced using only a portion of the isolated tissue. Based on this finding, the present inventors established the above-described procedure in which a portion of the isolated whole tumor tissue is not used, but various portions of the isolated whole tumor tissue are cut evenly and used to prepare the graft sample.

Then, the cut tissue was cut into small pieces using scissors and forceps. Then, the cut small tissue pieces were transferred into a tube, and minced using gentleMACS.

After the above-described mechanical dissociation process was performed, an enzymatic dissociation process was performed. The enzymatic dissociation process was performed by reacting the mechanically dissociated tissue sample with an enzyme mixture including papain and DNase in an incubator at 37° C. Herein, the enzyme mixture was used at a ratio of 1:1-1:2 relative to the volume of the tissue.

During establishment of the above-described enzymatic dissociation procedure, the present inventors have found that, DNase was used together with papain, the difficulty in cell dissociation caused by viscosity could be overcome. Based on this finding, the present inventors established an enzymatic dissociation procedure in which DNase is used together with papain.

After the enzymatic dissociation procedure as described above was performed, a filtration procedure was performed to obtain a single-cell population. In the filtration procedure, cell strainer filtration was used.

The obtained single-cell population was washed, and then subjected to Percoll gradient centrifugation at 20,000 rpm at 18° for 20 minutes to remove erythrocytes. After removal of erythrocytes, the number of cells in the sample was measured using a hemocytometer, and the viability of the cells was analyzed.

(2) Step of Orthotopically Transplanting Homogenized Graft Sample

The glioblastoma cell-containing sample resulting from step (1) was orthotopically transplanted into the brain of a mouse under the following conditions.

Specifically, 10 µl of HBSS (Hank's balanced salt solution) containing $1 \times 10^5$ to $2.0 \times 10^5$ cells was injected into the mouse brain. The mouse used was a NOG mouse. The sample was translated into the mouse brain at the location of 2 mm left and 1 mm anterior to the bregma, and 2 mm from the dura. The present inventors found that, when the number of cells transplanted into the mouse brain in this step was about $10^4$ or less or about $10^6$ or more and when the volume of the solution containing the cells was as too small as about 5 µl or less or as large as about 50 µl, the rate of production of a mouse model capable of mimicking the characteristics of the patient was reduced. Based on this finding, the present inventors established the optimum injection conditions as described above.

When the mouse transplanted with the cells showed a decrease in weight of 20% or more, it was sacrificed, and the brain was prepared into a specimen using a paraffin or freeze-sectioning method.

(3) Comparison with Conventional Technology

To demonstrate the superiority of the inventive method for producing the glioblastoma mouse model capable of mimicking the genetic and physiological characteristics of the patient, each step of the inventive method was compared with a conventional production method (comparative example), and the results of the comparison are shown in Table 2 below.

TABLE 2

| Order | Procedure | Comparative Example (conventional technology) | Example (present invention) | Effects |
|---|---|---|---|---|
| 1 | Selection of tissue to be used | Use of only a portion of whole tumor tissue | Use of homogenized whole tumor tissue | Use of the inventive method improves the rate of production of the glioblastoma mouse model and improves the similarity of the mouse model with the parental tumor |
| 2 | Tumor tissue dissociation (mechanical dissociation - and enzymatic dissociation) | Enzymatic treatment using papain | Enzymatic treatment using DNase1 in addition to papain | Use of the inventive method solves the difficulty in cell separation caused by increased viscosity after homogenization |
| 3 | Filtration of single cells | | | |
| 4 | Removal of erythrocytes | Use of Ficoll gradient | Use of Percoll gradient | Use of the inventive method improves the efficiency with which blood is removed |
| 5 | Calculation of cell number and viability | | | |
| 6 | Transplantation | Use of nude mouse | Use of NOG mouse | Use of the inventive method improves the rate of production of mouse models |
| | | Injection of 5-50 µl, and injection of about $10^4$ to $10^6$ cells | Injection of 10 µl, and injection of about $10^5$ cells | Use of the inventive method improves the rate of production of mouse models by the optimum injection conditions |

As described above, the present inventors developed the method in which the rate of production of the xenograft mouse model that properly reflects the genetic and physiological characteristics of the parental tissue is significantly high.

Example 3

Tissue Microarray and Immunohistochemistry

A tissue microarray was performed on parental glioblastoma and orthotopic xenograft tumors (PC-NS07-464, PC-NS08-493, PC-NS08-532, PC-NS08-559, PC-NS08-608, PC-NS09-626, PC-NS09-630, PC-NS09-633, PC-NS09-660, PC-NS09-690, and PC-NS09-696) derived therefrom.

Immunohistochemistry was performed using protein-specific antibodies (Ki-67, PCNA (DAKO), DLL3 (Santa Cruz), SOX2, Olig2, MAP2 (Abcam), MBP, PDGFA, EGFR (Santa Cruz), CHI3L1, TOP2A (LifeSpan Bioscience) and CD31, and BD Pharmingen for parental tumor).

Example 4

Short Tandem Repeat (STR) Genotyping, Array-Comparative Genomic Hybridization (aCGH) and Genetic Mutation Analysis of TP53 and IDH1

Genomic DNA was isolated from a tumor sample using the QIAamp DNA mini kit (QIAGEN). For STR genotyping, target DNA was amplified by multiplex PCR for 16 loci using the AmpFlSTR Identifier PCR Amplification Kit (Applied Biosystems). PCR products were mixed with an internal size standard (GS-500 LIZ, Applied Biosystems), and electrophoresed in an ABI 3130xL Genetic Analyzer. The electrophoresis results were analyzed with GeneMapper 4.0 software using the supplied allelic ladders (Applied Biosystems).

aCGH was performed using the Agilent Human Whole Genome CGH 244K microarray. For genetic mutation of TP53 and IDH1, PCR reactions (40 cycles, at 95° C. for 30 sec, 58° C. for 30 sec, and 72° C. for 30 sec) were carried out using 100 ng of gDNA, 200 nM each primer (Table 3 below), and Maxime PCR premix (iNtRON).

TABLE 3

Primers used in the sequence analysis of TP53 and IDH1

| Genes | Exon | Forward primers (5' → 3') | SEQ ID NOs: | Reverse primers (5' → 3') | SEQ ID NOs: | Product size |
|---|---|---|---|---|---|---|
| TP53 | Exon 5 | TTCACTTGTGCCCTGACTT | 1 | CTGGGCAACCAGCCCTGTC | 2 | 275 bp |
| TP53 | Exon 6 | ACCATGAGCGCTGCTCAGAT | 3 | AGTTGCAAACCAGACCTCAGGC | 4 | 236 bp |
| TP53 | Exon 7 | CTTGCCACAGGTCTCCCCAA | 5 | GAGGCTGGGGCACAGCAGGCCAGTG | 6 | 219 bp |
| TP53 | Exon 8 | ACTGCCTCTTGCTTCTCTTT | 7 | AAGTGAATCTGAGGCATAAC | 8 | 236 bp |
| IDH1 | Exon 4 | CGGTCTTCAGAGAAGCCAT | 9 | GCAAAATCACATTATTGCCAAC | 10 | 129 bp |

PCR products were purified by the QIAquick PCR purification kit, and bidirectional sequencing was performed using the BigDye Terminator v1.1 kit (Applied Biosystems) on the ABI 3130xl genetic analyzer (Applied Biosystems).

Example 5

Gene Expression Profiling

Gene expression profiling was conducted using Affymetrix Human Gene 1.0 ST arrays. The resulting CEL files were normalized using the Robust Multichip Averaging (RMA) procedure. A PM (perfect match)-MM (mismatch) difference model was used to obtain the expression values. The probe IDs were resolved into gene names by using GSEA-P program (downloadable from Broad Institute website).

For the REMBRANDT (Repository for Molecular Brain Neoplasia Data) data set, CEL files for high-grade glioma samples were downloaded from the website (https://cainte-grator.nci.nih.gov/rembrandt/), along with a matching clinical information file. The CEL files were processed in the same manner as the in-house produced CEL files, except that a matching array annotation file (for Affymetrix U133 Plus 2.0 array) was used.

For the TCGA data set (Cancer Genome Atlas Research Network, 2008), gene expression data files for 556 GBM samples originally produced using Affymetrix U133A 2.0 arrays were downloaded from the official website, along with a matching clinical information file. The gene expression files were provided in an already processed form (Level III).

Example 6

Glioblastoma (GBM) Subtype Prediction

Among the 840 marker genes originally used to classify GBM subtypes, 787 were represented in the microarray platform used. The 787 genes were annotated with the numeric code representing the unique subtype that each gene represents (1, 2, 3, and 4 for proneural, neural, classical, and mesenchymal markers, respectively, and 5 for the rest). The marker gene information file and the file containing the gene expression data for 58 GBM samples were loaded into Nearest Template Prediction module in GenePattern (available through Broad Institute). All samples were classified into one of the five categories with statistical significance (with Bonferroni p value below 0.05, bootstrap test with 1,000 resampling).

Example 7

Gene Signature Analysis

The 46 in-house-profiled GBM samples were subject to the tumorigenesis signature analysis. Genes differentially expressed (changes more than 1.5-fold) between the tumorigenic group (n=36) and the nontumorigenic group (n=10) were identified.

The tumorigenesis signature was composed of the differentially expressed genes, with each labeled with the associated subgroup and a value for log 2-fold change. The signature was loaded into the Nearest Template Prediction module in GenePattern. Also, either the REMBRANDT or the TCGA data set in GCT format was loaded into the module. The module produced an output file with classification of samples in each data set.

Survival analysis (Kaplan-Meier plot and log rank test) was performed using R Survival package. For permutation analysis, the present inventors randomly regrouped the GBM patients into tumorigenesis and nontumorigenesis subgroups, maintaining the size of the original subgroups. A "control" signature was derived and applied to the REMBRANDT data set for prognostic prediction. The fraction of the resulting 500 p values (from log rank test) smaller than the original p value of the unshuffled data set (p=0.000046) was defined as the p value of the permutation test.

Example 8

Pathway Analysis (1) Identification of the In Vivo Tumorigenesis-Associated Pathways The 46 in-house-profiled GBM samples were subject to pathway analysis by using the GSEA-P program. The analysis utilized gene sets in MSigDB v3.0, specifically gene sets that are derived from three major manually-curated pathway databases: KEGG, REACTOME, and BIOCARTA. Genes were ranked and weighted by the degree of differential expression, quantified by Z scores (adjusted from T scores of t test).

For the permutation-type parameter, an alternative option (gene_set) was used instead of the default option (phenotype). This alternative setting tends to give more generous p values. However, the default setting is likely to give excessively conservative significance assessments when the number of samples is small, and most of the pathways that pass the significance cutoff only at the alternative setting showed the expected trend of correlation with patient survival in the REMBRANDT data set.

(2) Quantification of Pathway Activity from a Gene Expression Data Set

For the REMBRANDT data set, expression values were "gene-normalized". Specifically, for each gene, the log expression value for each sample was offset by the average log expression value of the gene across all the samples. To calculate the activity of a given pathway in a given sample, the relative expression values of the pathway genes were compared to the relative expression values of all genes. KS score (Python Stats package) was used for the comparison; the score is defined between −1 and 1, with the value bigger and smaller than 0 indicates the pathway genes are up- and downregulated, respectively, compared to all genes in the given sample.

R survival package was used to (1) plot patient survival of samples up- and down-regulating a given pathway, (2) assess statistical significance of the difference in survival between the two groups, and (3) calculate hazard ratio of the KS score (pathway activity) for OS (by the Cox proportional hazard regression).

Experimental Example 1:

In Vitro Cultures and Orthotopic Xenograft Tumor Model

As shown in FIG. 1, 71 surgical specimens were collected from 59 GBM patients (from 11 patients, both primary and recurrent tumor specimens were acquired; from one patient, two recurrent specimens with no primary sample were acquired).

In order to produce orthotopic xenograft tumor models from the specimens, the glioblastoma tissue of each specimen was dissociated into single cells as shown in Example 2 above, and the single cells were stereotactically injected into the brains of immunodeficient NOD/SCID Il2rg$^{-/-}$ (NOG) mice within 12 hr after surgery.

In parallel, in vitro growth kinetics of the freshly isolated GBM cells were determined by culturing them in serum-free media containing EGF and bFGF. Because clonogenic growth as neurospheres is an in vitro indicator of self-renewal in GBM stem cells, sphere formation (diameter: R50 mm) was used as the readout for in vitro growth of GBMs. In vivo tumorigenicity was defined as the formation of tumor within 12 months after tumor cell injection. Due to technical issues including the limited number of cells available, the present inventors could not test one sample for in vivo tumorigenic potential and 21 samples for in vitro sphere formation capacity (FIG. 1).

Figure 2:
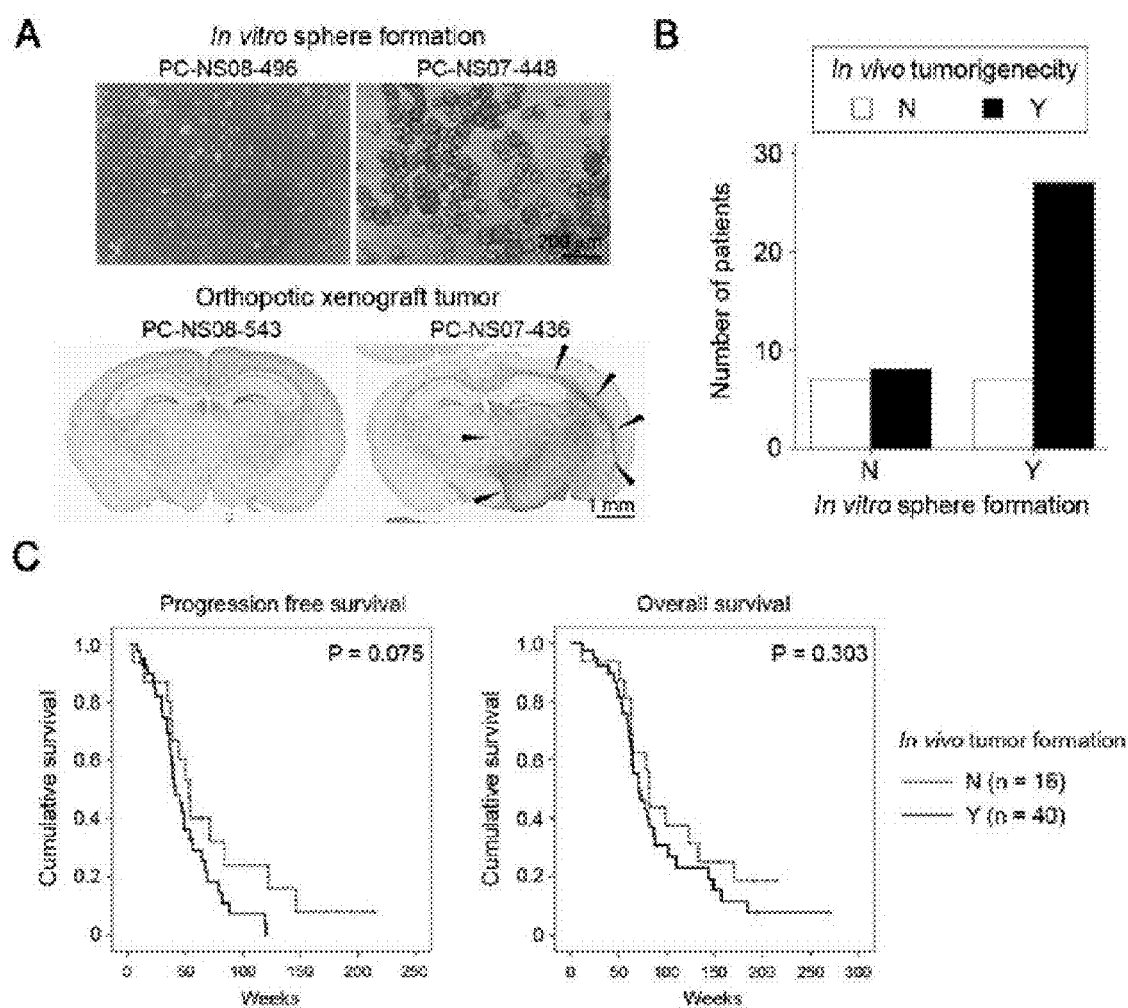
FIG. 2 shows primary cultures and orthotopic xenograft animal models derived from glioblastoma surgical samples. (A) Acutely dissociated GBM cells were primarily cultured in the NBE condition, or stereotactically injected into the brains of immunodeficient mice. Immunohistochemistry against PCNA was illustrated for orthotopic xenograft tumors. The arrowheads indicate the border of a PCNA-positive xenograft tumor. (B) The correlation between the in vitro sphere formation capacity and in vivo tumorigenicity of acutely dissociated glioblastoma cells was analyzed by the Fisher's exact test (p=0.09). (C) The PFS (progressive-free survival) and OS (overall survival) of the glioblastomas with in vivo tumorigenic potential (n=40) were compared with those without the potential (n=16) by using the Kaplan-Meier plots and log rank test.

With this paralleled in vivo xenograft tumors and in vitro short-term cultures, the present inventors determined a potential correlation between the two. In vivo xenograft tumor formation was histopathologically confirmed in 53 cases from 70 samples (75.7%). Robust in vitro sphere formation and sustained growth was confirmed in 34 cases from 50 samples (68.0%) (FIGS. 1 and 2A).

The above results indicate that there is a positive correlation between the in vivo xenograft tumor and the in vitro culture.

Experimental Example 2

Examination of Morphologic and Pathologic Similarity

The utility of orthotopic GBM xenografts as a model system of human GBM in situ would be greatly increased if the glioblastoma xenograft mice produced in the present invention tumors precisely reflect the morphologic and pathologic characteristics of their parental tumors. In the following experiment, the present inventors compared the morphological and pathological similarity between the parental tumor and the xenograft tumor in terms of three parameters: invasiveness, proliferation index, and vessel intensity.

Figure 3:
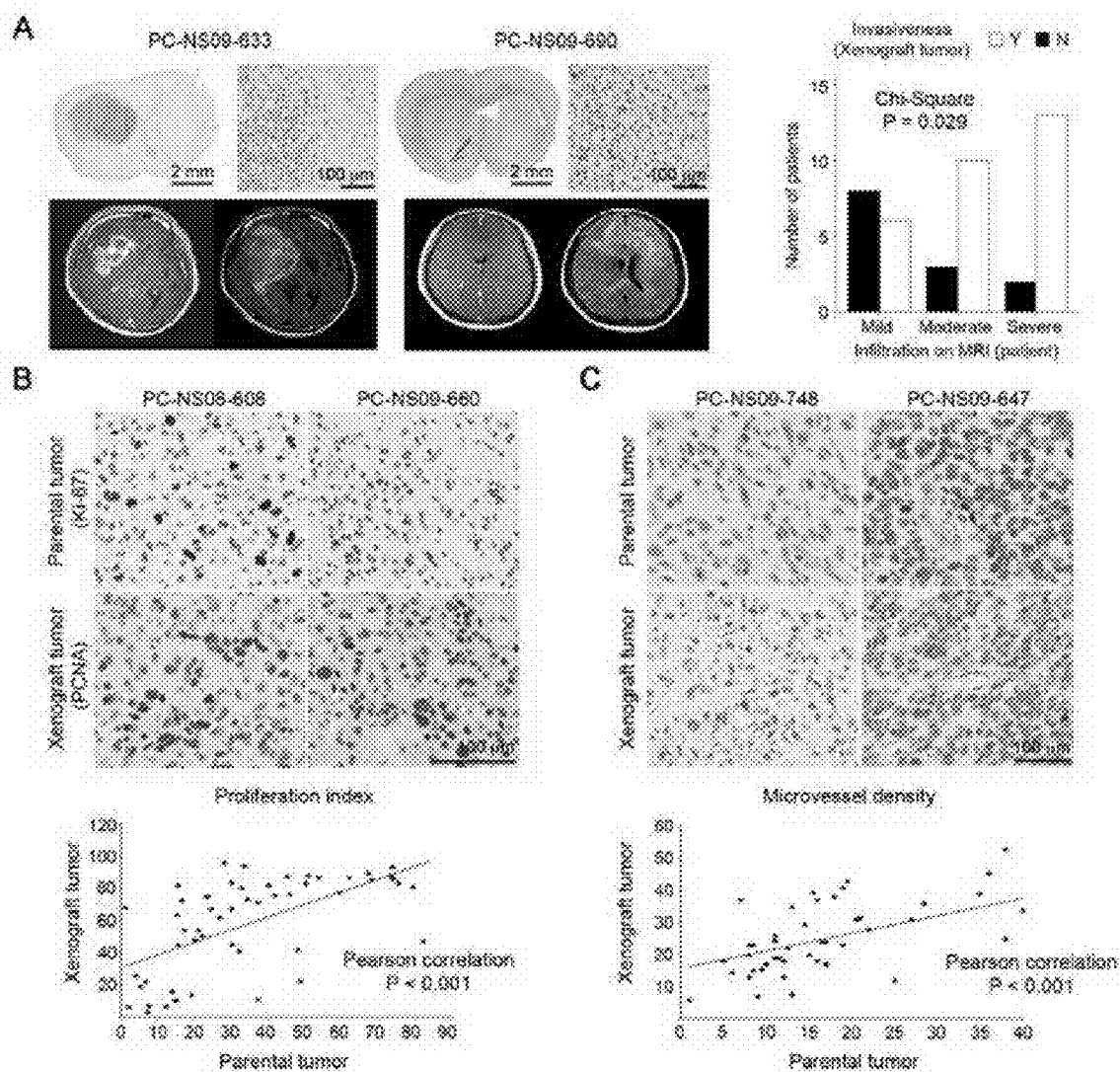
FIG. 3 is a representation of morphologic and pathologic characteristics of parental GBMs by the corresponding orthotopic xenograft tumors. The invasiveness (A), proliferation index (B), and microvessel density (C) of the parental and corresponding orthotopic xenograft tumors were analyzed and compared. (A) The invasive parental and xenograft tumor was defined by comparisons of the distances of infiltration with the diameters of main mass in MRI and pathologic sections, respectively. (B) Proliferation index was analyzed by immunohistochemistry against Ki-67 (parental GBMs) or PCNA (xenograft GBMs), and then calculated as the number of positive cells from 100 cells selected randomly. Each index was analyzed three times and the average was utilized for the statistical analysis. (C) Microvessel density was analyzed by immunohistochemistry against CD31. Three microscopic fields were randomly selected at 200× magnification, and the numbers of CD31-positive microvessels were calculated. The averages of the three values were utilized for the statistical analysis.
Figure 4:
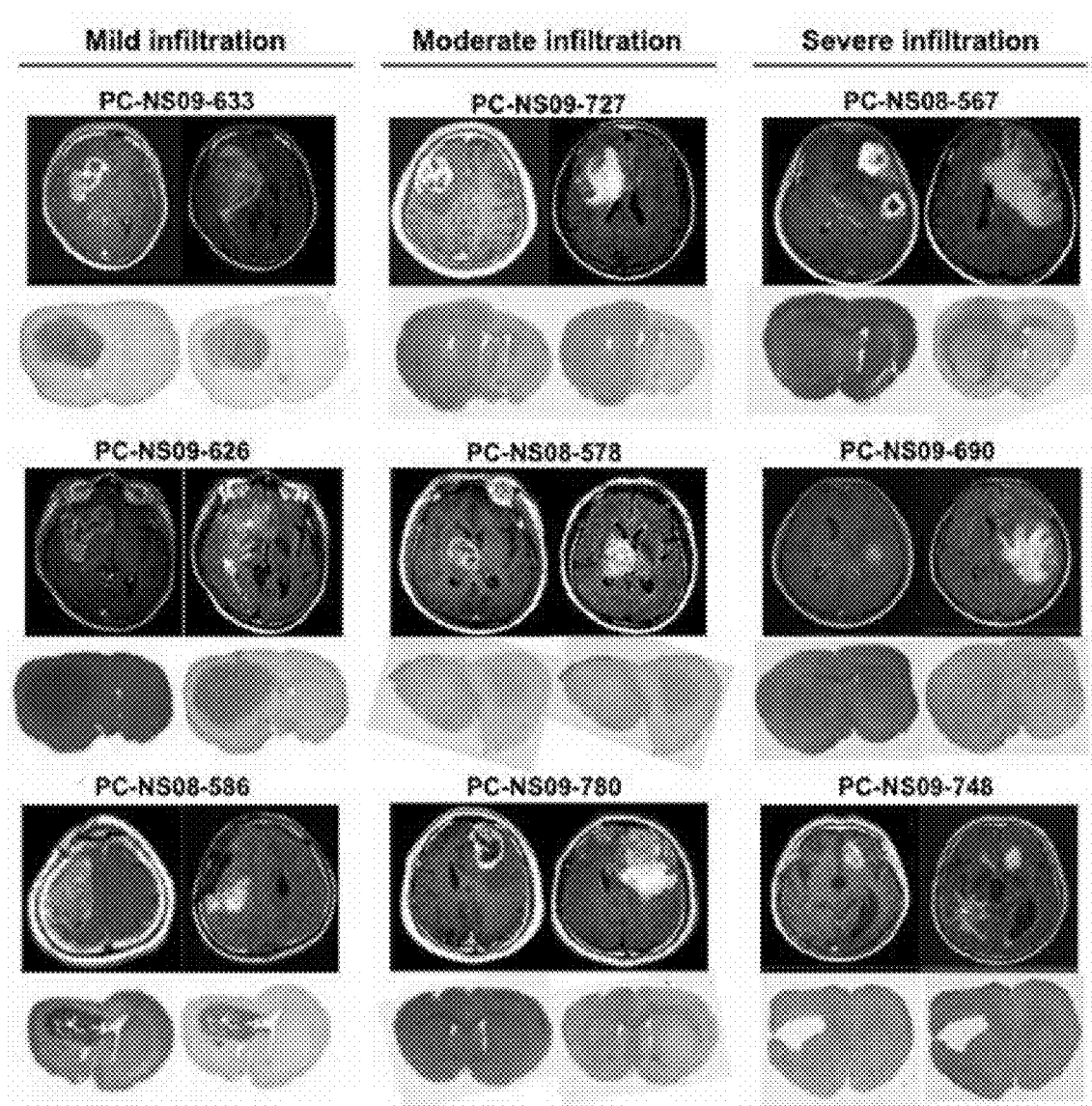
FIG. 4 shows the infiltration of parental tumors on MRI and the invasiveness of orthotopic xenograft tumors. The invasiveness of the parental tumors was analyzed using MRI T2/FLAIR images according to the response assessment in neuro-oncology (RANO) criteria. The invasiveness of patient's tumors was defined as follows: 0="no invasion," 1 (mild)="distance of invasion<2×diameter of tumor mass," 2 (moderate)="2×diameter of tumor mass<distance of invasion<3×diameter of tumor mass," and 3 (severe)="3×diameter of tumor mass<distance of invasion." The invasiveness of orthotopic xenograft tumors was defined as Y="distance of infiltration>2×diameter of main mass" in paraffin sections. Three MRI scan images of parental tumors and histology of corresponding orthotopic xenograft tumors were provided for each mild, moderate, or severe infiltration.

(1) Invasiveness (FIGS. 3A and 4): the invasiveness of each parental tumor was analyzed using MRI T2/FLAIR images according to the response assessment in neuroon-cology (RANO) criteria, and a numerical score for invasiveness was allocated comparing distance of invasion with diameter of tumor (FIG. 1). Interestingly, comparison of the patient MRI and invasiveness of xenograft tumors revealed that invasiveness of parental and corresponding xenograft tumors were significantly correlated (n=42, Chi-square test, 23 P=0.029).

(2) Proliferation index (FIG. 3B): the proliferation index of xenograft tumors was positively correlated with that of their parental tumors (n=53, Pearson correlation, p<0.001).

(3) Microvessel density (FIG. 3C): the CD31-positive microvessel density of xenograft tumors showed significant positive correlation with that of their parental tumors (n=53, Pearson correlation, p<0.001).

The above results support that the glioblastoma xenograft mouse model produced by the inventive method sufficiently reflect the morphological and pathological conditions of the parental tumor, suggesting that the mouse model can be used to screen a patient-specific drug and test the effect and side effect of the drug before direct application of the drug to the patient before phase 2 clinical trials.

Experimental Example 3

Genomic Similarity

To further examine the similarities between parental tumors and the corresponding orthotopic xenograft tumors, genomic analysis was performed.

First, the present inventors performed short tandem repeat (STR) genotyping to ensure that each GBM xenograft was derived from the specific patient (FIG. 5A).

In addition, analysis of array-comparative genomic hybridization (aCGH) and genetic mutation was performed, and the results of the analysis indicated that all examined genomic alterations found in the parental GBMs including copy number variations and genetic mutations were precisely replicated in the corresponding xenograft tumors (FIGS. 5B and 5C).

It is known that a recent large genomic study categorized GBMs into four subgroups (proneural, neural, classical, and mesenchymal) based on their distinct gene expression signatures (Cancer Genome Atlas Research Network, 2008 Nature 455, 1061-1068.; Phillips et al., 2006 Cancer Cell 9, 157-173.; Verhaak et al., 2010 Cancer Cell 17, 98-110.). In order to determine whether the inventive library covers the full spectrum of these subtypes and test whether gene expression signatures of a parental tumor are maintained in the orthotopic xenograft tumor, the present inventors performed global gene expression profiling analysis.

Specifically, the present inventors analyzed 58 GBM patient's surgical specimens, for which microarray gene expression data were available (FIG. 1). The present inventors also performed tissue microarray (TMA) analysis that encompasses the parental GBMs and corresponding orthotopic xenograft tumors. For the subtype determination, the present inventors adopted the nearest template prediction algorithm (Hoshida, 2010) for single-sample-based determination of subtypes. The analysis identified 18 proneural, 6 neural, 13 classical, and 19 mesenchymal GBMs in the data set (two undetermined; FIGS. 1 and 5D).

On tissue microarray (TMA) sections, the present inventors performed a series of immunohistochemical analysis against distinct GBM subtype markers: DLL3, SOX2, and Olig2 (proneural); MBP (neural); PDGFA and EGFR (proneural); CHI3L1, MAP2, and TOP2A (mesenchymal).

As a result, it was found that preferential expression of each subtype marker proteins was detected both in the parental GBM specimens and the corresponding xenograft tumors (FIG. 5E).

The above results suggest that the orthotopic xenograft mouse models and their parental tumors have genetic similarity.

Experimental Example 4

Studies on Functional Relevance

The results of Experimental Examples 1 to 4 revealed that the orthotopic xenograft mouse models and their parental tumors have similar genetic, morphological and physiological characteristics. Further, the present inventors examined whether the patient-specific response to standard glioblastoma therapies could be replicated in the orthotopic xenograft tumor models.

(1) Radiation Therapy

In order to examine functional relevance for radiotherapy, the present inventors arbitrarily chose five patients who had received radiation-treatment in the clinic after resection of primary tumors (four from inventive library, one from our recently published study ["827," PFS=128 weeks] [Son et al., 2009 Cell Stem Cell 4, 440-452.)], and subjected their corresponding xenograft tumors to in vivo whole brain irradiation (2Gy daily for 5 days). Survival of the mice bearing PC-NS07-448, PC-NS07-464, PC-NS08-578, PC-NS09-780, and 827 tumors was differentially increased by the radiation therapy (21.9%±7.1%, 49.8%±14.1%, 45.9%±8.6%, 23.3%±19.5%, and 45.0%±5.9%, respectively, FIGS. 6A and 7A).

The increment of survival was positively correlated with the PFS of the parental tumors (FIG. 6A). Specifically, radiation-mediated survival benefits of the mice bearing the GBMs (PC-NS07-448 and PC-NS09-780) whose parental tumors have relatively short-PFS, are significantly less than those of the other GBMs with longer PFS (FIG. 6A). This result suggests that the radiation-response of the parental GBM can be predicted using the xenograft tumor model of the present invention.

To further elucidate clinical implications of the differential response to the radiation therapy, the present inventors derived Radio-Response (RR) signature by comparing gene expression alteration of the radioresistant PC-NS07-448 ("448") and radiosensitive PCNS07-464 ("464") xenograft tumors after the radiation therapy. The results are shown in Table 4 below and FIG. 7B.

TABLE 4

| Term | Count | P value | Fold Enrichment |
|---|---|---|---|
| RR genes (upregulated) | | | |
| oxphos (ES: 1.195) | | | |
| GO:0000302~response to reactive oxygen species | 3 | 0.01 | 19.326 |
| GO:0007568~aging | 3 | 0.02 | 13.177 |
| GO:0006979~response to oxidative stress | 3 | 0.042 | 8.838 |
| GO:0010035~response to inorganic substance | 3 | 0.063 | 7.07 |
| GO:0033554~cellular response to stress | 4 | 0.102 | 3.414 |
| GO:0009719~response to endogenous stimulus | 3 | 0.193 | 3.579 |
| GO:0010033~response to organic substance | 3 | 0.426 | 2.01 |
| RR genes (downregulated) | | | |
| chromatin assmebly (ES: 2.147) | | | |
| GO:0031497~chromatin assembly | 5 | 0 | 14.669 |
| GO:0065004~protein-DNA complex assembly | 5 | 0 | 14.024 |
| GO:0006323~DNA packaging | 5 | 0.001 | 10.908 |
| GG:0006333~chromatin assembly or disassembly | 5 | 0.001 | 10.049 |
| GO:0006334~nucleosome assembly | 4 | 0.004 | 12.155 |
| GO:0034728~nucleosome organization | 4 | 0.005 | 10.978 |
| GO:0051276~chromosome organization | 7 | 0.01 | 3.684 |
| GO:0006325~chromatin organization | 6 | 0.015 | 4.052 |
| GO:0034622~cellular macramolecular complex assembly | 5 | 0.034 | 4.013 |
| GO:0034621~cellular macromolecular complex subunit organization | 5 | 0.048 | 3.575 |
| GO:0065003~macromolecular complex assembly | 6 | 0.111 | 2.303 |
| GO:0043933~macromolecular complex subunit organization | 6 | 0.136 | 2.157 |
| development (ES: 1.188) | | | |
| GO:0008585~female gonad development | 3 | 0.025 | 11.965 |
| GO:0046545~development of primary female sexual characteristics | 3 | 0.029 | 11.098 |
| GO:0046660~female sex differentiation | 3 | 0.029 | 11.098 |
| GO:0008406~gonad development | 3 | 0.069 | 6.837 |
| GO:0003006~reproductive developmental process | 4 | 0.079 | 3.897 |
| GO:0048608~reproductive structure development | 3 | 0.084 | 6.077 |
| GO:0045137~develpment of primary sexual characteristics | 3 | 0.086 | 6.029 |

TABLE 4-continued

| Term | Count | P value | Fold Enrichment |
|---|---|---|---|
| GO:0007548~sex differentiation | 3 | 0.114 | 5.071 |
| GO:0048609~reproductive process in a multicellular organism | 5 | 0.117 | 2.621 |
| GO:0032504~multicellular organism reproduction | 5 | 0.117 | 2.621 |
| radiation (ES: 1.18) | | | |
| GO:0010165~response to X-ray | 3 | 0.001 | 51.049 |
| GO:0010212~response to ionizing radiation | 3 | 0.022 | 12.762 |
| GO:0006302~double-strand break repair | 3 | 0.024 | 12.351 |
| GO:0006259~DNA metabolic process | 6 | 0.044 | 3.027 |
| GO:0033554~cellular response to stress | 6 | 0.065 | 2.706 |
| GO:0009314~response to radiation | 3 | 0.179 | 3.829 |
| GO:0006281~DNA repair | 3 | 0.298 | 2.696 |
| GO:0009628~response to abiotic stimulus | 3 | 0.415 | 2.081 |
| GO:0006974~response to DNA damage stimulus | 3 | 0.422 | 2.053 |
| JNK cascade (ES: 1.055) | | | |
| GO:0007254~JNK cascade | 3 | 0.022 | 12.979 |
| GO:0031098~stress-activated protein kinase signaling pathway | 3 | 0.024 | 12.155 |
| GO:0033554~cellular response to stress | 6 | 0.065 | 2.706 |
| GO:0000165~MAPKKK cascade | 3 | 0.157 | 4.162 |
| GO:0007242~intracellular signaling cascade | 8 | 0.204 | 1.626 |
| GO:0007243~protein kinase cascade | 3 | 0.418 | 2.07 |

Based on the gene expression, high-grade gliomas in the REMBRANDT data set (n=463, Madhavan et al., 2009 Mol. Cancer Res. 7, 157-167) were clustered into a 448-like group (n=267) and a 464-like group (n=196) (FIG. 74B). When the samples were restricted to 219 GBMs (grade IV), 174 and 45 GBMs were clustered into a 448-like group and a 464-like group, respectively. Both the 448-like high-grade gliomas and GBMs showed significantly worse clinical outcome than the 464-like group (FIG. 7B), confirming the clinical relevance of the RR signature.

(2) Chemotherapy

It is known that GBM patients differentially respond to the TMZ-based chemotherapy depending on the methylation status of the MGMT gene promoter. Thus, the present inventors tested whether the differential response could be reproduced in the xenograft mouse models of the present invention.

In agreement with the clinical observation, TMZ chemotherapy prolonged the OS of mice with MGMT-methylated PC-NS07-464 tumors (148.5%±45.4%, FIG. 6B) significantly more than that of mice harboring MGMT-unmethylated PCNS09-559 tumors (55.7%±38.6%, p<0.001, FIG. 6B). These results were consistent with clinical results.

(3) Targeted Therapy

Figure 6:
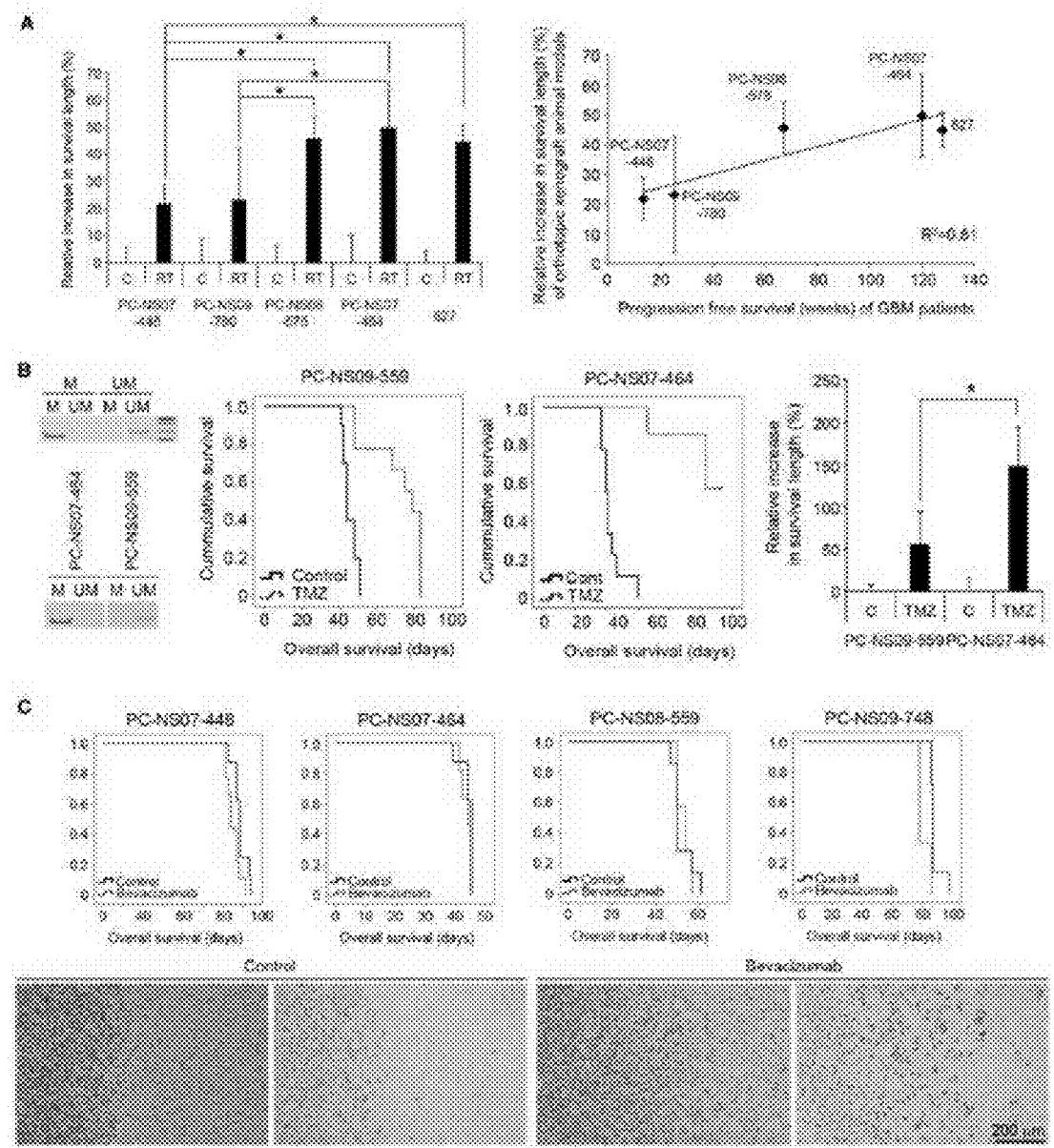
FIG. 6 shows a comparison of treatment responsiveness between parental tumors and corresponding orthotopic xenograft tumors. (A) Xenograft tumors derived from PC-NS07-448, PC-NS07-464, PC-NS08-578, PC-NS09-780, or 827 tumor (n=8, 15, 9, 9, and 4 for the control group; n=9, 9, 10, 9, and 4 for the radiation group, respectively) were treated with whole brain radiation therapy (2Gy daily for 5 days since 50% median survival time passed). Overall survival (OS) was calculated, and the increase in the survival length by the whole brain irradiation was shown (left, *p<0.05). The increase in the survival length of xenograft tumors was correlated with the PFS of parental tumors (right). Error bar represents SD. (B) The methylation status of the MGMT promoter was analyzed by methylation specific PCR (left, M, methylation specific primers or methylated control gDNA; UM, methylation specific primers or unmethylated control gDNA). Xenograft tumors derived from PC-NS07-464 or PC-NS09-559 (n=9 and 10 for the control (C) group, n=7 and 9 for the TMZ group, respectively) were treated with TMZ (65 mg/kg/day, oral administration). Overall survival (OS) was calculated, and the increase in the survival length by the TMZ chemotherapy was shown. *p<0.05. (C) Xenograft tumors derived from PC-NS07-448, PC-NS07-464, PC-NS09-559, or PC-NS09-748 (n=8, 8, 7, and 7 for the control group, and n=9, 11, 7, and 6 for the Bevacizumab group, respectively) were treated with Bevacizumab (10 mg/kg, intraperitoneal injection, twice per week). The morphologic alteration of the xenograft tumors by Bevacizumab treatment was analyzed by H&E staining and immunohistochemistry against human nuclei (low, PCNS07-464).
Figure 7:
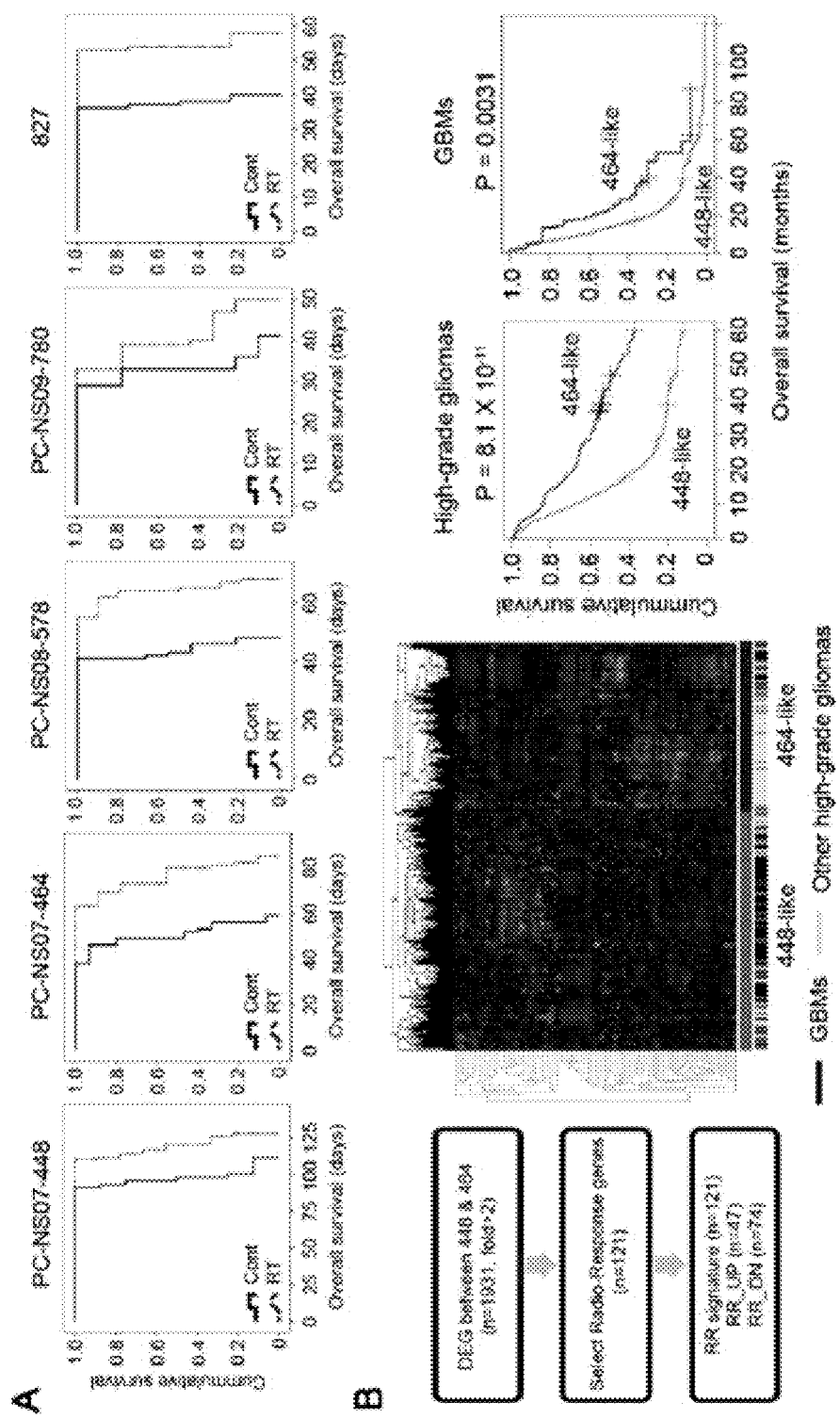
FIG. 7 shows in vivo whole brain irradiation to xenograft orthotopic tumors and the RR (radiation-response) signature. (A) Xenograft tumors derived from PC-NS07-448, PC-NS07-464, PC-NS08-578, PC-NS09-780, or 827 tumor [n=8, 15, 9, 9, and 4 for the control group, and n=9, 9, 10, 9, and 4 for the radiation group, respectively] were treated with whole brain radiation therapy (2Gy daily for 5 days). The effects of irradiation on survival length were analyzed by the Kaplan-Meier plot and log-rank test. (B) The RR signature was defined from mRNA expression analysis of PC-NS07-448 and PC-NS07-464 xenograft tumors that had in vivo radiation therapy (left). Based on the RR signature, high-grade gliomas of the REMBRANDT data set were hierarchically clustered into the 448-like and 464-like groups. The overall survival (OS) of high-grade gliomas and the OS of GBMs of the 448-like or 464-like group were analyzed by the Kaplan-Meier plot and log-rank test.

The hypervascular nature of GBMs has suggested that antiangiogenic treatment, such as the VEGF-neutralizing antibody, bevacizumab, may have beneficial activity. Although it showed treatment effects on the animal model using a conventional GBM cell line, such as U-87MG, it failed to elongate the OS of GBM patients compared to that of standard treatment controls. Accordingly, the present inventors tested the antitumor activity of bevacizumab, and the results of the test are shown in FIG. 6.

As a result, the survival of mice with PC-NS07-448, PC-NS07-464, PC-NS08-559, or PC-NS09-748 xenograft tumors was not altered by bevacizumab treatment (FIG. 6C). Also, although the OS was not altered, the treatment made xenograft tumors more invasive (FIG. 6C). These morphological changes were also observed in human GBMs with bevacizumab treatment, which suggest that xenograft tumors derived from GBM surgical samples would predict the results of clinical trial.

Experimental Example 5

Genetic Signature of In Vivo Tumorigenic Potential

Figure 8:
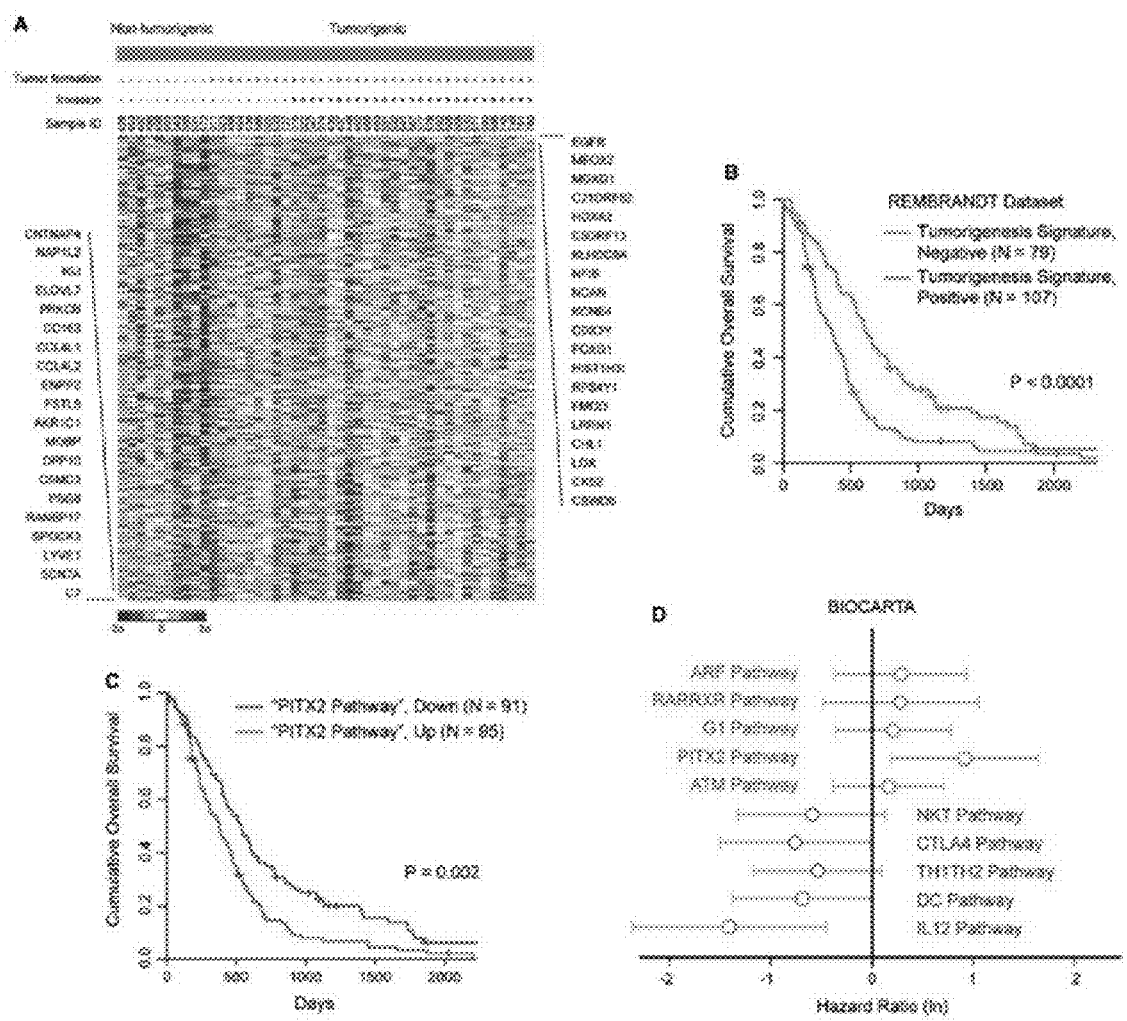
FIG. 8 shows the tumorigenesis signature, tumorigenesis-associated pathways, and their association with clinical outcome in an independent data set. (A) Expression of 709 genes that are differentially expressed (cutoff, change more than 1.5-fold) between 10 nontumorigenic and 36 tumorigenic GBMs, plotted as a heat map (two-dimensional graph) after row-normalization. Red and blue indicate high and low expression, respectively. The 20 genes most highly differentially expressed with each group are listed on the sides. (B) A Kaplan-Meier plot comparing cumulative OS of two groups of patients in the REMBRANDT data set, with each group either positively or negatively associated with the tumorigenesis signature. (C) A Kaplan-Meier plot comparing the OS of two groups of patients in the REMBRANDT data set, with each group either up- or down-regulating the PITX2 pathway. (D) A forest plot displaying hazard ratios (in a natural log scale) and their 95% confidence intervals, with each hazard ratio representing the correlation between the calculated activity of a given pathway and the OS of patients in the REMBRANDT data set. The top five and bottom five entries correspond to the pathways in BIO-CARTA that were found most up- and down-regulated, respectively, in the group positively associated with the tumorigenesis signature.

The above results indicated that the in vivo tumorigenic potential of primarily cultured GBM cells is associated with clinical aggressiveness of the corresponding patients. Thus, the present inventors defined the "tumorigenesis" signature composed of 709 differentially expressed genes (change more than 1.5-fold) between tumorigenic GBMs (n=36; FIG. 1) and nontumorigenic GBMs (n=10) (FIG. 8A).

In order to validate this signature, the present inventors applied this to two independent GBM gene expression profiling data sets, TCGA and REMBRANDT. Nearest template prediction algorithm allowed for prediction of each GBM patient into two groups, each either positively or negatively associated with the tumorigenesis signature.

When patient survival was compared between the two groups, the positive-group showed significantly worse survival than the negative-group with the REMBRANDT data set (p<0.0001, log rank test; FIG. 8B).

Figure 9:
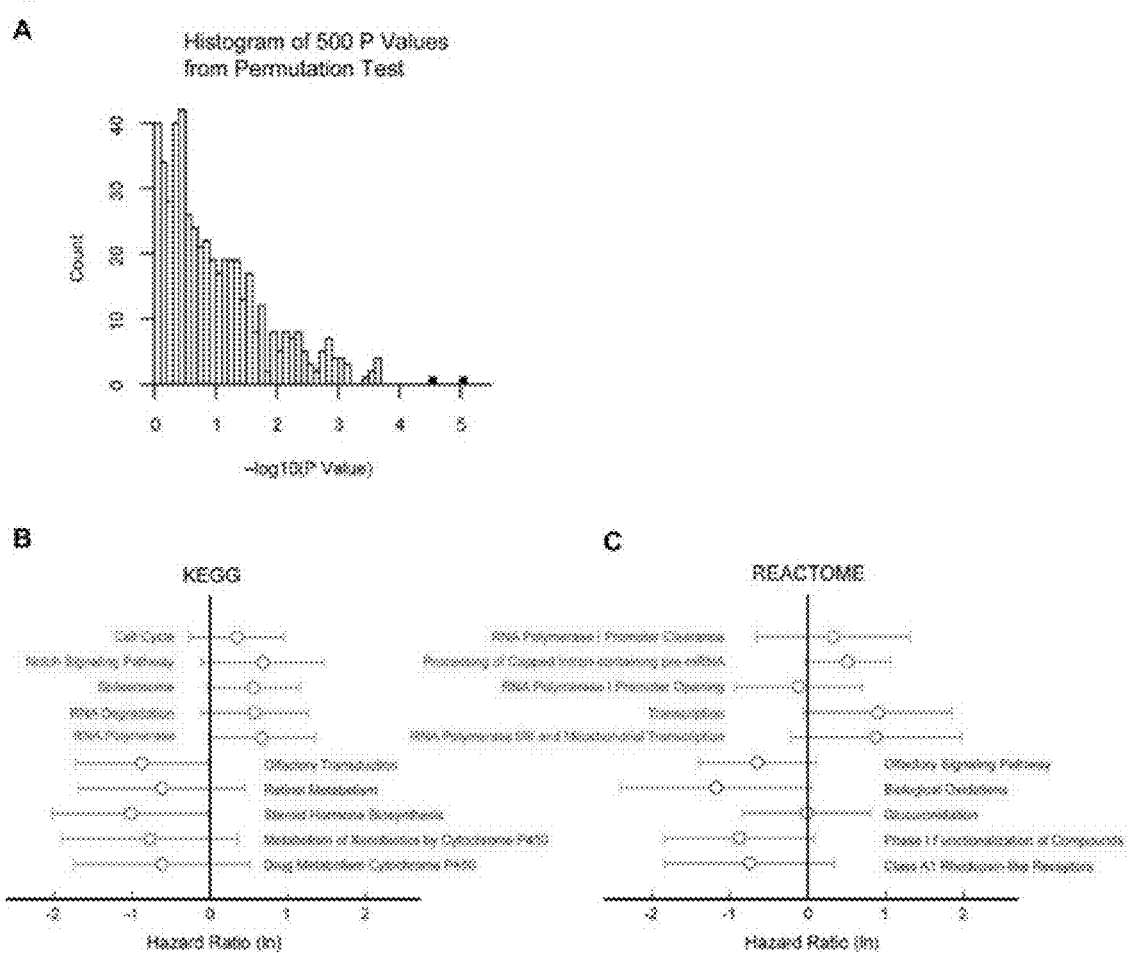
FIG. 9 shows permutation analysis and the association between the tumorigenesis-associated pathways and clinical outcome in an independent data set. (A) Distribution of the P values from the 500 permutation analyses. In each analysis, a "control" signature was generated, and the performance of each control signature in predicting patient survival of the REMBRANDT data set was quantified as a log-rank test P value. Two (marked as solid bars) of the 500 log-rank test P values were smaller than the P value (0.000046) of the original signature, which makes the permutation test P value 0.004 (=2/500). (B) A forest plot for KEGG-annotated pathways. (C) A forest plot for REACTOME-annotated pathways.

In addition, permutation analysis indicated that such or more severe separation in survival is unlikely observed by chance (p=0.004), potentiating the validity of the signature (FIG. 9A). The statistically significant trend was also observed with the TCGA data set (p=0.019).

In order to investigate the biological underpinnings of the differential tumorigenic potential and the clinical aggressiveness, the present inventors turned to pathway analysis using GSEA (gene set enrichment analysis: Clark and Ma'ayan, 2011 Sci. Signal. 4, tr4; Subramanian et al., 2005 Proc. Natl. Acad. Sci. USA 102, 15545-15550).

The analysis revealed that pathways related to cell cycle, telomere maintenance, transcription, Notch signaling, or Wnt signaling were upregulated in the GBMs with in vivo tumorigenic potential, whereas pathways related to neuronal or immune functions were downregulated.

If these pathways influence clinical aggressiveness in GBMs, the activity of the pathways can be used to predict patient survival. Thus, the present inventors devised a method of calculating pathway activity for each patient based on the gene expression profile. Specifically, the pathway activity was defined between −1 and 1, with the score bigger than 0 and smaller than 0 indicating up- and downregulation, respectively. When the pathway activity for the PITX2 pathway (PITX2 is a transcription factor, acting downstream of WNT) was calculated for each patient of the REMBRANDT data set, the present inventors detected that the ones upregulating the pathway corresponds to the ones with poorer survival (p=0.002, log-rank test; FIG. 8C).

Alternatively, by Cox proportional hazard regression, high pathway activity was significantly correlated with poor patient survival (p=0.007, one-sided Wald test; FIG. 8D). When this analysis was expanded to five most highly upregulated and downregulated pathways in the BIOCARTA (FIG. 8D), KEGG (FIG. 9B), and REACTOME (FIG. 9C) databases, the present inventors observed the significant trend that the pathways upregulated or downregulated in the GBMs with in vivo tumorigenic potential are correlated with poor or favorable patient survival, respectively (p<0.05 for all three databases, KS test).

As the GBMs that made invasive tumors (n=29) in the mouse brain showed significantly worse clinical outcomes in the data set of the present invention, when compared to those that made noninvasive tumors (n=13) or did not made tumors (n=16), the present inventors sought for the opportunity to further stratify tumorigenic GBMs based on their differential invasiveness. Thus, the present inventors compared gene expression of the "invasive" (n=29) and "demarcated" (n=13) groups.

Figure 10:
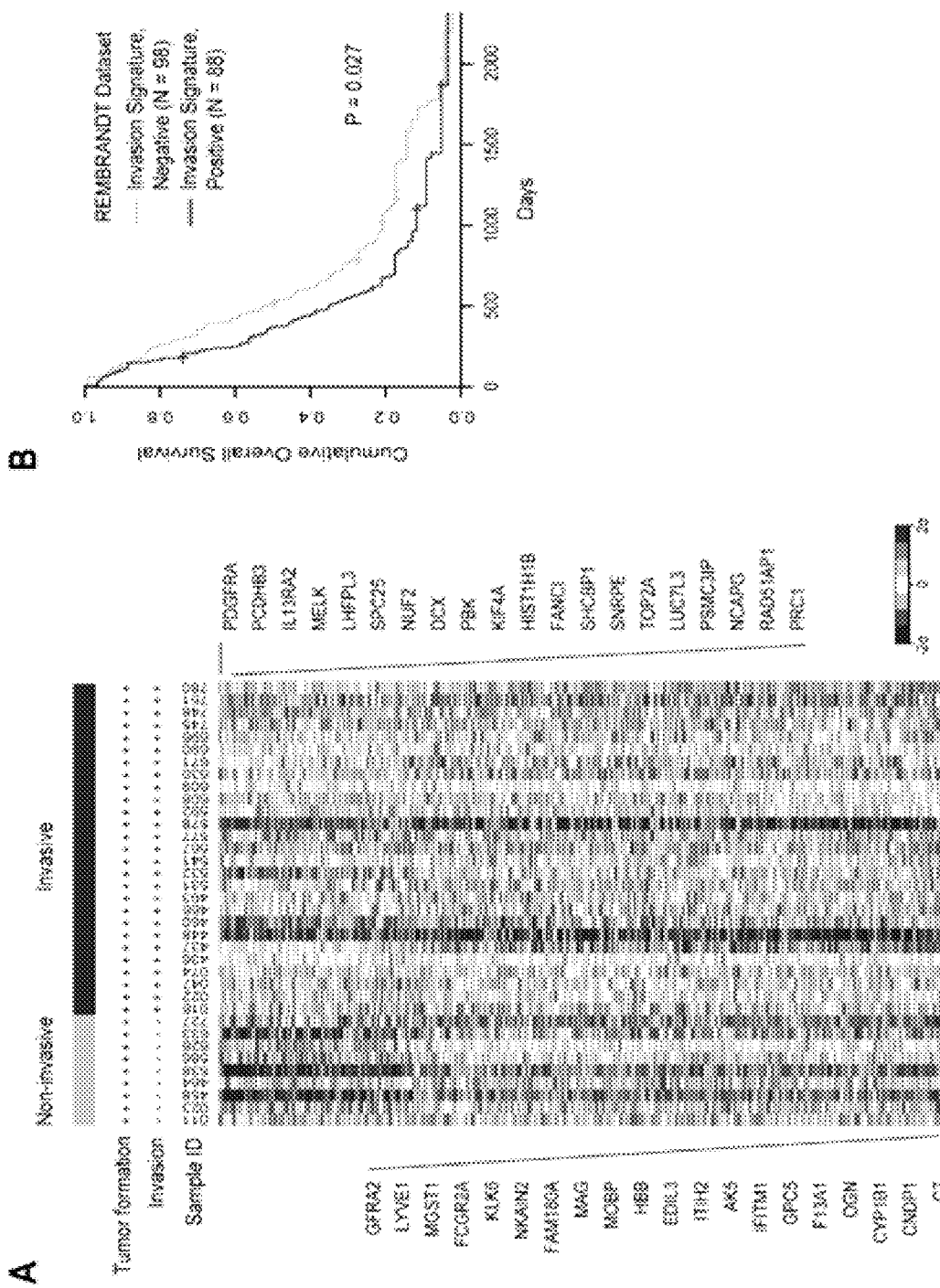
FIG. 10 shows the invasion signature and their association with clinical outcome in an independent data set. (A) Expression of 777 genes that are differentially expressed (change more than 1.5 fold) between 9 and 27 GBMs that made non-invasive and invasive tumors in the mouse brain, respectively, plotted as a heat map after row-normalization. The 20 genes most highly differentially expressed with each group are listed on the sides. (B) A Kaplan-Meier plot comparing cumulative OS of two groups of patients in the REMBRANDT data set, with each group either positively or negatively associated with the invasive signature.

As a result, it was shown that 777 differentially expressed genes (change more than 1.5-fold; FIG. 10) had the "invasive" signature (FIG. 10). To validate this signature, the present inventors again used the REMBRANDT data sets, as did for the tumorigenesis signature. When patient survival time was compared between the two groups, the invasive group showed significantly worse survival than the demarcated group (p=0.027, log-rank test; FIG. 10B), suggesting possible clinical relevance of the invasion signature.

INDUSTRIAL APPLICABILITY

A patient-specific glioblastoma mouse model according to the present invention has a glioblastoma showing the same morphological and genetic characteristics as those of a glioblastoma patient, and thus can be effectively used for the screening of a patient-specific glioblastoma therapeutic agent. Specifically, when the mouse model according to the present invention is used, a patient-specific therapeutic agent can be effectively screened, because the patient's response to a candidate therapeutic agent, and the effect and side effect of the candidate agent can be predicted. In addition, the patient-specific glioblastoma mouse model can be used in preclinical translational research for predicting clinical test results, and particularly, can be used in a phase 1.5 clinical trial (after a phase 1 clinical trial, but before a phase 2 clinical trial) for selecting patients and predicting medicinal effects.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for producing a glioblastoma mouse model comprising the steps of:
   (a) dividing a whole glioblastoma tissue, isolated from a patient, into 4 or more sections, collecting one or more pieces from each of the 4 or more sections, and homogenously mixing the collected pieces to prepare a homogenous mixture of the glioblastoma tissue pieces collected from each of the 4 or more sections of the whole glioblastoma tissue;
   (b) dissociating single cells of glioblastoma including glioblastoma stem cells from the homogenously mixed glioblastoma tissue pieces by sequentially performing mechanical dissociation and enzymatic dissociation with an enzyme mixture including protease and DNase;
   (b)' removing erythrocytes by Percoll gradient centrifugation from a graft sample, which contains the glioblastoma cells as single cells obtained in step (b); and
   (c) orthotopically transplanting a graft sample comprising $1\times10^5$ to $2.0\times10^5$ glioblastoma cells obtained in step (b) in a volume of 5-10 μl, into the brain of an immunodeficient mouse by injecting the sample into the brain at the location of 1.5-2.5 mm left and 0.5-1.5 mm anterior to the bregma and 1.8-2.2 mm deep from the dura.

2. The method of claim 1, wherein each of the one or more pieces has a volume of 1-8 mm$^3$ and is collected from the 4 or more sections of the glioblastoma tissue in step (a).

3. The method of claim 1, wherein the volume of the mixture of the pieces collected in step (b) is 30-100% of the volume of the glioblastoma tissue isolated from the patient.

4. The method of claim 1, wherein the immunodeficient mouse is NOG (NOD/Shi-scid, IL-2Ry KO) mouse.

5. The method of claim 1, wherein the glioblastoma mouse model shows the same genetic and morphological characteristics as those of glioblastoma of the patient.

* * * * *